United States Patent [19]

Eicken et al.

[11] Patent Number: 5,480,897
[45] Date of Patent: Jan. 2, 1996

[54] ANILIDE DERIVATIVES AND THEIR USE FOR COMBATING BOTRYTIS

[75] Inventors: Karl Eicken, Wachenheim; Norbert Goetz, Worms; Albrecht Harreus, Ludwigshafen; Eberhard Ammermann, Heppenheim; Gisela Lorenz, Neustadt; Harald Rang, Ludwigshafen, all of Germany

[73] Assignee: BASF Aktiengesellschaft, Ludwigshafen, Germany

[21] Appl. No.: 215,463

[22] Filed: Mar. 21, 1994

Related U.S. Application Data

[62] Division of Ser. No. 973,976, Nov. 9, 1992, Pat. No. 5,330,995.

[30] Foreign Application Priority Data

Nov. 22, 1991 [DE] Germany .......................... 41 38 387.7
Feb. 18, 1992 [DE] Germany .......................... 42 04 764.1
Feb. 18, 1992 [DE] Germany .......................... 42 04 766.8
Feb. 18, 1992 [DE] Germany .......................... 42 04 767.6
Feb. 18, 1992 [DE] Germany .......................... 42 04 768.4

[51] Int. Cl.⁶ .................... A01N 43/78; C07D 277/24; C07D 277/28
[52] U.S. Cl. .................... 514/365; 548/200; 548/205
[58] Field of Search .................... 548/200, 205; 514/365, 371

[56] References Cited

U.S. PATENT DOCUMENTS 3,709,992  1/1973  von Schneling et al. .......... 514/371
3,725,427  4/1973  Harrison et al. .................. 548/200
3,883,658  5/1975  Phillips et al. .................... 424/270
4,153,703  5/1979  Harrison et al. .................. 424/270
4,427,688  1/1984  Rentzen et al. .................... 548/200
4,837,242  6/1989  Ohsumi et al. .................... 548/200
4,877,802  10/1989 Wilson et al. ..................... 514/365
4,992,434  2/1991  Topfl et al. ....................... 514/212
5,045,554  9/1991  Alt et al. .......................... 514/365

FOREIGN PATENT DOCUMENTS 0057776  5/1981  Japan .
9101311  2/1991  WIPO .

Primary Examiner—Richard L. Raymond
Assistant Examiner—Deborah Lambkin
Attorney, Agent, or Firm—Oblon, Spivak, McClelland, Maier & Neustadt

[57] ABSTRACT

The use of nicotinic anilide derivatives of the general formula

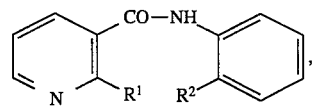

where the substituents have the following meanings:

$R^1$ halogen, methyl, trifluoromethyl, methoxy, methylthio, methylsulfinyl, methylsulfonyl $R^2$ unsubstituted or halogen-substituted alkyl, unsubstituted or halogen-substituted alkenyl, alkynyl, unsubstituted or halogen-substituted alkoxy, unsubstituted or halogen-substituted alkenyloxy, alkynyloxy, cycloalkyl, cycloalkenyl, cycloalkyloxy, cycloalkenyloxy for combating Botrytis, and nicotinic anilides of the formula I.

11 Claims, No Drawings

ANILIDE DERIVATIVES AND THEIR USE FOR COMBATING BOTRYTIS

This is a division, of application Ser. No. 07/973,976, filed on Nov. 9, 1992, U.S. Pat. No. 5,330,995.

The present invention relates to the use of anilide derivatives of the general formula

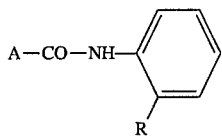

where A has the following meanings:

pyridin-3-yl substituted in the 2-position by halogen, methyl, trifluoromethyl, methoxy, methylthio, methylsulfinyl or methylsulfonyl, phenyl substituted in 2-position by methyl, trifluoromethyl, chlorine, bromine or iodine, 2-methyl-5,6-dihydropyran-3-yl, 2-methyl- 5,6-dihydro-1,4-oxathiin-3-yl, 2-methyl-5,6-dihydro-1,4oxathiin-3-yl-4-oxide, 2-methyl-5,6-dihydro-1,4-oxathiin-3-yl-4,4-dioxide; 2-methyl-furan-3-yl substituted in the 4- and 5-positions by hydrogen or methyl; thiazol-5-yl substituted in the 2- and 4-positions by hydrogen, methyl, chlorine or trifluoromethyl; thiazol-4-yl substituted in the 2- and 5-positions by hydrogen, methyl, chlorine or trifluoromethyl; 1-methylpyrazol- 4-yl substituted in the 3- and 5-positions by methyl, chlorine or trifluoromethyl; or oxazol-5-yl substituted the 2- and 4-positions by hydrogen, methyl or chlorine, and R has the following meanings: unsubstituted or halogen-substituted $C_2$–$C_{12}$-alkyl, unsubstituted or halogen-substituted $C_3$–$C_{12}$-alkenyl, $C_3$–$C_6$-alkynyl, unsubstituted or halogen-substituted $C_2$–$C_{12}$-alkoxy, unsubstituted or halogen-substituted $C_3$–$C_{12}$-alkenyloxy, $C_3$–$C_{12}$-alkynyloxy, unsubstituted or $C_1$–$C_4$-alkyl-substituted $C_3$–$C_6$-cycloalkyl, unsubstituted or $C_1$–$C_4$-alkyl-substituted $C_4$–$C_6$-cycloalkenyl, unsubstituted or $C_1$–$C_4$-alkyl-substituted $C_5C_6$-cycloalkyloxy, unsubstituted or $C_1$–$C_4$-alkyl-substituted $C_5C_6$-cycloalkenyloxy, or phenyl which is unsubstituted or substituted by $C_1$–$C_4$-alkyl, $C_1$–$C_4$-alkoxy, $C_1$–$C_4$-alkylthio or halogen, for combating Botrytis.

The present invention further relates to novel anilide derivatives.

It is known to use nicotinic anilides, e.g., 2-chloronicotic-2'-ethylanilide (US 4,001,416) and 2-chloronicotic-3'-isopropyl-anilide (DE 26 11 601), as fungicides.

We have now found that the anilide derivatives defined at the outset have a good action on Botrytis.

In view of their action, those compounds are preferred in which the substituents have the following meanings:

halogen, e.g., fluorine, chlorine and bromine, alkyl, especially ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethyl-butyl, 2-ethylbutyl, 1-ethyl-2-methylpropyl, n-heptyl, 1-methylhexyl, 1-ethylpentyl, 2-ethylpentyl, 1-propylbutyl, octyl, decyl or dodecyl, where alkyl may bear from one to three of the above-mentioned halogen atoms, especially fluorine and chlorine, alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl- 2-propenyl, 1-ethyl-2-propenyl, 2-hexenyl, 3hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, especially 2-propenyl, 2-butenyl, 3-methyl-2-butenyl and 3-methyl-2-pentenyl, where alkenyl may bear from one to three of the abovementioned halogen atoms, especially fluorine and chlorine, alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,2-dimethyl-2-butynyl, 1,1-dimethyl-3-butynyl, 1,2-dimethyl-3-butynyl, 2,2-dimethyl3-butynyl, 1-ethyl-2-butynyl, 1-ethyl-3-butynyl, 2-ethyl-3-butynyl and 1-ethyl-1-methyl-2-propynyl, alkoxy, especially ethoxy, propoxy, 1-methylethoxy, butoxy, 1-methylpropoxy, 2-methylpropoxy, 1,1-dimethylethoxy, n-pentyloxy, 1-methylbutoxy, 2-methylbutoxy, 3-methylbutoxy, 1,2-dimethylpropoxy, 1,1-dimethylpropoxy, 2,2-dimethylpropoxy, 1-ethylpropoxy, n-hexyloxy, 1-methylpentyloxy, 2-methylpentyloxy, 3-methylpentyloxy, 4-methylpentyloxy, 1,2-dimethylbutoxy, 1,3-dimethylbutoxy, 2,3-dimethylbutoxy, 1,1-dimethylbutoxy, 2,2-dimethylbutoxy, 3,3-dimethylbutoxy, 1,1,2-trimethylpropoxy, 1,2,2-trimethylpropoxy, 1-ethylbutoxy, 2-ethylbutoxy, 1-ethyl-2-methylpropoxy, n-heptyloxy, 1-methylhexyloxy, 2-methylhexyloxy, 3-methylhexyloxy, 4-methylhexyloxy, 5-methylhexyloxy, 1-ethylpentyloxy, 2-ethylpentyloxy, 1-propylbutyloxy, octyloxy, decyloxy, and dodecyloxy, where alkoxy may bear from one to three of the above-mentioned halogen atoms, especially fluorine and chlorine, alkenyloxy such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-3-butenyloxy, 1-ethyl-2-butenyloxy, 1-ethyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy and 1-ethyl-2-methyl-2-propenyloxy, especially 2-propenyloxy, 2-butenyloxy, 3-methyl-2-butenyloxy and 3-methyl-2-pentenyloxy; where alkenyloxy may bear from one to three of the above-mentioned halogen atoms, especially fluorine and chlorine;

alkynyloxy such as 2-propynyloxy, 2-butynyloxy, 3-butynyloxy, 1-methyl-2-propynyloxy, 2-pentynyloxy, 3-pentynyloxy, 4-pentynyloxy, 1-methyl-3-butynyloxy, 2-methyl-3-butynyloxy, 1-methyl-2-butynyloxy, 1,1-dimethyl-2-propynyloxy, 1-ethyl-2-propynyloxy, 2-hexynyloxy, 3-hexynyloxy, 4-alkynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-4-pentynyloxy, 4-methyl-3-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy and 1-ethyl-1-methyl-2-propynyloxy, preferably 2-propynyloxy, 2-butynyloxy, 1-methyl-2-propynyloxy and 1-methyl-2-butynyloxy, $C_3$–$C_6$-cycloalkyl, such as cyclopropyl, cyclobutyl, cyclotpentyl and cyclohexyl, where cycloalkyl is unsubstituted or substituted by one to three $C_1$–$C_4$-alkyl radicals;

$C_4$–$C_6$-cycloalkenyl, such as cyclobutenyl, cyclopentenyl and cyclohexenyl, which is unsubstituted or substituted by one to three $C_1$–$C_4$-alkyl radicals;

$C_5$–$C_6$-cycloalkoxy such as cyclopentyloxy or cyclohexyloxy, which may be substituted by one to three $C_1$–$C_4$-alkyl radicals;

$C_5$–$C_6$-cycloalkenyloxy such as cyclopentyloxy or cyclohexaryloxy, which may be substituted by one to three $C_1$–$C_4$-alkyl radicals.

For combating Botrytis, the use of nicotinic anilide derivatives of the formula I in which the substituents have the meanings given below is preferred:

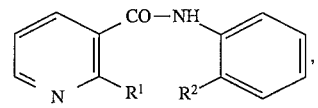

$R^1$ halogen, methyl, trifluoromethyl, methoxy, methylthio, methylsulfinyl, methylsulfonyl $R^2$ unsubstituted or halogen-substituted $C_2$–$C_{12}$-alkyl, unsubstituted or halogen-substituted $C_3$–$C_{12}$-alkenyl, $C_3$–$C_6$-alkynyl, unsubstituted or halogen-substituted $C_2$–$C_{12}$-alkoxy, unsubstituted or halogen-substituted $C_3$–$C_{12}$-alkenyloxy, $C_3$–$C_{12}$-alkynyloxy, $C_3$–$C_6$-cycloalkyl, $C_4$–$C_6$-cycloalkenyl, $C_5$–$C_6$-cycloalkyloxy, $C_5$–$C_6$-cycloalkenyloxy.

The compounds of the formula I are obtained for instance by reacting a correspondingly substituted nicotinic halide of the formula 2

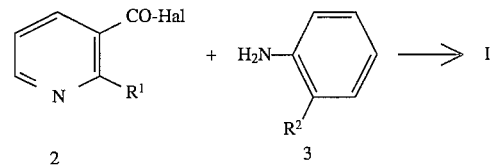

Hal denoting chlorine or bromine, with an ortho-substituted aniline of the formula 3 in the presence of a base. The nicotinic acids and their halides of the formula 2 are known. The anilines of the formula 3 are known or can be prepared by known methods (Helv. Chim. Acta 60, 978 (1977); Zh. Org. Khim 26, 1527(1990); Heterocyclus 26, 1885 (1987); Izv. Akad. Nauk. SSSR Ser. Khim 1982, 2160).

Compounds of the formula I in which $R^1$ is chlorine and $R^2$ has the meanings given above are particularly preferred.

TABLE 1

Compounds of the formula I

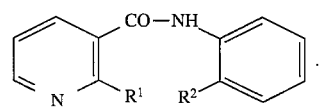

| No. | R1 | R2 | Phys. data m.p. [°C.] |
|---|---|---|---|
| 1.1 | F | n-$C_3H_7$ | |
| 1.2 | F | i-$C_3H_7$ | |
| 1.3 | F | sec.-$C_4H_9$ | 52–54 |
| 1.4 | F | i-$C_4H_9$ | 87–89 |
| 1.5 | Cl | n-$C_3H_7$ | 103–104 |
| 1.6 | Cl | n-$C_4H_9$ | |
| 1.7 | Cl | sec.-$C_4H_9$ | 94–96 |
| 1.8 | Cl | i-$C_4H_9$ | 99–101 |
| 1.9 | Cl | tert.-$C_4H_9$ | 118–120 |
| 1.10 | Cl | n-$C_5H_{11}$ | |
| 1.11 | Cl | sec.-$C_5H_{11}$ | |

TABLE 1-continued

Compounds of the formula I

![Structure of formula I: pyridine with CO-NH linkage to phenyl, R1 on pyridine, R2 on phenyl] I

| No. | R1 | R2 | Phys. data m.p. [°C.] |
|---|---|---|---|
| 1.12 | Cl | n-C$_6$H$_{13}$ | |
| 1.13 | Cl | n-C$_7$H$_{15}$ | |
| 1.14 | Cl | sec.-C$_7$H$_{15}$ | |
| 1.15 | Cl | n-C$_8$H$_{17}$ | |
| 1.16 | Cl | n-C$_{10}$H$_{23}$ | |
| 1.17 | Cl | n-C$_{12}$H$_{25}$ | |
| 1.18 | Cl | 1-Methylvinyl | 90–91 |
| 1.19 | Cl | 2-Methylvinyl | |
| 1.20 | Cl | Allyl | |
| 1.21 | Cl | 2-Methylallyl | |
| 1.22 | Cl | 2-Ethylallyl | |
| 1.23 | Cl | 1-Methylallyl | |
| 1.24 | Cl | 1-Ethylallyl | |
| 1.25 | Cl | 1-Methyl-2-butenyl | |
| 1.26 | Cl | 1-Ethyl-2-butenyl | |
| 1.27 | Cl | 1-Isopropyl-2-butenyl | |
| 1.28 | Cl | 1-n-Butyl-2-butenyl | |
| 1.29 | Cl | 1-Methyl-2-pentenyl | |
| 1.30 | Cl | 1,4-Dimethyl-2-pentenyl | |
| 1.31 | Cl | Propargyl | |
| 1.32 | Cl | 2-Butynyl | |
| 1.33 | Cl | 3-Butynyl | |
| 1.34 | Cl | Ethoxy | 131–132 |
| 1.35 | Cl | Propoxy | |
| 1.36 | Cl | 1-Methylethoxy | 65–67 |
| 1.37 | Cl | n-Butoxy | 84–85 |
| 1.38 | Cl | 1-Methylpropoxy | 72–74 |
| 1.39 | Cl | 2-Methylpropoxy | 81–84 |
| 1.40 | Cl | 1,1-Dimethylethoxy | |
| 1.41 | Cl | n-Pentyloxy | |
| 1.42 | Cl | n-Hexyloxy | |
| 1.43 | Cl | n-Hepyloxy | |
| 1.44 | Cl | n-Octyloxy | |
| 1.45 | Cl | 2-Ethylhexyloxy | |
| 1.46 | Cl | n-Decyloxy | |
| 1.47 | Cl | 2-Propenyloxy | 86–88 |
| 1.48 | Cl | 2-Butentyloxy | 92–95 |
| 1.49 | Cl | 2-Methyl-2-propenyloxy | 75–76 |
| 1.50 | Cl | 2-Pentenyloxy | |
| 1.51 | Cl | 3-Pentenyloxy | |
| 1.52 | Cl | 3-chloro-2-propenyloxy | |
| 1.53 | Cl | 2,3-Dichloro-2-propenyloxy | |
| 1.54 | Cl | 2,3,3-Trichloro-propenyloxy | |
| 1.55 | Cl | 2-Propynyloxy | 79–84 |
| 1.56 | Cl | 2-Butynyl-oxy | |
| 1.57 | Cl | 3-Butynyl-oxy | |
| 1.58 | Cl | 1-Methyl-2-propynyloxy | |
| 1.59 | Cl | Cyclopropyl | 144–145 |
| 1.60 | Cl | Cyclobutyl | |
| 1.61 | Cl | Cyclopentyl | 112–114 |
| 1.62 | Cl | Cyclohexyl | 141–142 |
| 1.63 | Cl | 2-Cyclopentenyl | 123–124 |
| 1.64 | Cl | 1-Cyclopentenyl | |
| 1.65 | Cl | 2-Cyclohexenyl | 92–93 |
| 1.66 | Cl | 1-Cyclohexenyl | |
| 1.67 | Cl | Cyclopentyloxy | 80–82 |
| 1.68 | Cl | Cyclohexyloxy | |
| 1.69 | Cl | 2-Cyclopentenyloxy | |
| 1.70 | Cl | 2-Cyclohexenyloxy | oil |
| 1.71 | Br | sec.-Butyl | |
| 1.72 | Br | i-Butyl | |
| 1.73 | CH$_3$ | sec.-Butyl | |
| 1.74 | CH$_3$ | i-Butyl | |
| 1.75 | CF$_3$ | i-Propyl | |
| 1.76 | CF$_3$ | sec.-Butyl | |
| 1.77 | CF$_3$ | i-Butyl | |
| 1.78 | OCH$_3$ | i-Propyl | |

TABLE 1-continued

Compounds of the formula I

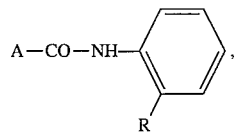

| No. | R1 | R2 | Phys. data m.p. [°C.] |
|---|---|---|---|
| 1.79 | OCH₃ | sec.-Butyl | oil NMR 0.8t(3H); 1.2d (3H); 1.6m(2H); 3.0q(1H); 4.1s(3H); 7.2m(3H); 7.3m (1H); 8.3m(1H); 8.4m(1H), 9.8s(1H) |
| 1.80 | OCH₃ | i-Butyl | oil NMR 0.8d(6H); 1.9m (1H); 2.5d(2H), 4.05s(3H), 7.2m(4H); 7.5d(1H); 8.3d (1H); 8.4m(1H); 9.8s(1H) |
| 1.81 | SCH₃ | i-Propyl | |
| 1.82 | SCH₃ | sec.-Butyl | 89–91 |
| 1.83 | SCH₃ | i-Butyl | 140–141 |
| 1.84 | SO₂CH₃ | sec.-Butyl | 191–192 |
| 1.85 | SO₂CH₃ | i-Butyl | 150–153 |
| 1.86 | Cl | 2-Ethylpropoxy | 65–66 |
| 1.87 | Cl | 3-Methyl-3-butenyloxy | 83–84 |

MANUFACTURING EXAMPLES

Example 1

At 0° C., 3.5 g of 2-chloroonicotic chloride is dripped into a solution of 2.7 g of 2-n-propylaniline and 2.0 g of triethylamine in 30 ml of tetrahydrofuran, and the mixture is stirred for 2 hours at 0° C. After dilution with 300 ml of water, there is isolated 3.2 g of 2-chloronicotic acid-2-n-propylanilide; m.p.: 103°–104° C. (No. 1.5).

Example 2

4.4 g of 2-chloroonicotic acid-2-sec.-butylanilide (Table 1, No. 7) is refluxed for 2 hours in a solution of 5.5 g of 30% strength sodium methylate solution in 20 ml of methanol. After dilution with 250 ml of water the mixture is extracted twice, each time with 100 ml of ethyl acetate. From the combined organic phases there is isolated, after drying and evaporation of the solvent, 3.8 g of 2-methoxy-nicotinic acid-2-sec.-butylanilide as an oil (No. 1.79).

Example 3

Similarly to Example 1, there is obtained from 5.7 g of 2-methylthionicotic chloroide, 4.6 g of 2-sec-butylaniline and 3.1 g of triethylamine 6.6 g of 2-methylthionicotic acid-2-sec.-butylanilide; m.p.: 89°–91° C. (No. 1.82).

Example 4

While stirring at 35° C., 2.20 g of 30% strength hydrogen peroxyde is dripped into a mixture of 2.00 g of the above-mentioned product (Example 3) in 5 ml of glacial acetic acid and 0.13 g of sodium tungstate, and the mixture is stirred for 3 hours at 35° C. After dilution with 15 ml of water, removal of the crystals by suction filtration, washing with water and drying, there is obtained 1.7 g of 2-methylsulfonylnicotic acid-2-sec.-butylanilide; m.p.: 191°–192° C. (No. 1.84).

The invention further relates to the use of anilide derivatives of the formula II

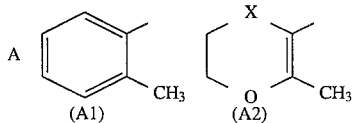

where the substituents have the following meanings:

X methylene or sulfur

R unsubstituted or halogen-substituted $C_3$–$C_{12}$-alkyl, unsubstituted or halogen-substituted $C_3$–$C_{12}$-alkenyl, $C_3$–$C_6$-alkynyl, unsubstituted or halogen-substituted $C_2$–$C_{12}$-alkoxy, unsubstituted or halogen-substituted $C_3$–$C_{12}$-alkenyloxy, $C_3$–$C_{12}$-alkynyloxy, unsubstituted or $C_1$–$C_4$-alkyl-substituted $C_3$–$C_6$-cycloalkyl, unsubstituted or $C_1$–$C_4$-alkyl-substituted $C_4$–$C_6$-cycloalkenyl, unsubstituted or $C_1$–$C_4$-alkyl-substituted $C_5$–$C_6$-cycloalkyloxy, unsubstituted or $C_1$–$C_4$-alkyl-substituted $C_5$–$C_6$-cycloalkenyloxy for combating Botrytis.

The compounds of the formula 2 are obtained for instance by reacting a correspondingly substituted carboxylic halide of the formula 4 with an ortho-substituted aniline of the formula 3 in the presence of a base:

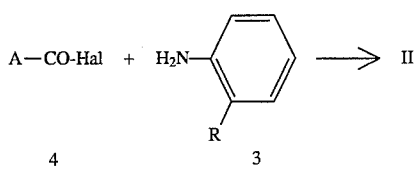

Hal is chlorine or bromine.

The carboxylic acids and their halides $ACO_2H$ and $A\text{-}CO\text{-}Hal$ (4) are known.

TABLE 2

Compounds of the formula II

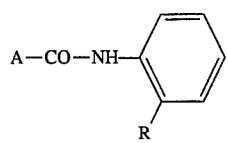

| No. | A | R | X | Phys. data mp [°C.] |
|---|---|---|---|---|
| 2.1 | $A_1$ | $i\text{-}C_3H_7$ | — | 108–109 |
| 2.2 | $A_1$ | $n\text{-}C_3H_7$ | — | 112–114 |
| 2.3 | $A_1$ | $n\text{-}C_4H_9$ | — | |
| 2.4 | $A_1$ | $sec.\text{-}C_4H_9$ | — | 89–90 |
| 2.5 | $A_1$ | $i\text{-}C_4H_9$ | — | 118–11 |
| 2.6 | $A_1$ | $tert.\text{-}C_4H_9$ | — | |
| 2.7 | $A_1$ | $n\text{-}C_5H_{11}$ | — | |
| 2.8 | $A_1$ | $sec.\text{-}C_5H_{11}$ | — | |
| 2.9 | $A_1$ | $n\text{-}C_6H_{13}$ | — | |
| 2.10 | $A_1$ | $n\text{-}C_7H_{15}$ | — | |
| 2.11 | $A_1$ | $sec.\text{-}C_7H_{15}$ | — | |
| 2.12 | $A_1$ | 1-Methylvinyl | — | |
| 2.13 | $A_1$ | 2-Methylvinyl | — | |
| 2.14 | $A_1$ | Allyl | — | |
| 2.15 | $A_1$ | 2-Methylallyl | — | |
| 2.16 | $A_1$ | 2-Ethylallyl | — | |
| 2.17 | $A_1$ | 1-Methylallyl | — | |
| 2.18 | $A_1$ | 1-Ethylallyl | — | |
| 2.19 | $A_1$ | 1-Methyl-2-butenyl | — | |
| 2.20 | $A_1$ | 1-Ethyl-2-butenyl | — | |
| 2.21 | $A_1$ | 1-Isopropyl-2-butenyl | — | |
| 2.22 | $A_1$ | 1-n-Butyl-2-butenyl | — | |
| 2.23 | $A_1$ | 1-Methyl-2-pentenyl | — | |
| 2.24 | $A_1$ | 1,4-Dimethyl-2-pentenyl | — | |
| 2.25 | $A_1$ | Propargyl | — | |
| 2.26 | $A_1$ | 2-Butynyl | — | |
| 2.27 | $A_1$ | 3-Butynyl | — | |
| 2.28 | $A_1$ | Ethoxy | — | |
| 2.29 | $A_1$ | Propoxy | — | |
| 2.30 | $A_1$ | 1-Methylethoxy | — | |
| 2.31 | $A_1$ | n-Butoxy | — | |
| 2.32 | $A_1$ | 1-Methylpropoxy | — | 46–84 |
| 2.33 | $A_1$ | 2-Methylpropoxy | — | |
| 2.34 | $A_1$ | 1,1-Dimethylethoxy | — | |
| 2.35 | $A_1$ | n-Pentyloxy | — | |
| 2.36 | $A_1$ | n-Hexyloxy | — | |
| 2.37 | $A_1$ | 2-Ethylhexyloxy | — | |
| 2.38 | $A_1$ | 2-Propenyloxy | — | |
| 2.39 | $A_1$ | 2-Butentyloxy | — | 62–66 |
| 2.40 | $A_1$ | 2-Methyl-2-propenyloxy | — | oil |
| 2.41 | $A_1$ | 2-Pentenyloxy | — | |
| 2.42 | $A_1$ | 3-Pentenyloxy | — | |
| 2.43 | $A_1$ | 3-Chloro-2-propenyloxy | — | |
| 2.44 | $A_1$ | 2,3-Dichloro-2-propenyloxy | — | |
| 2.45 | $A_1$ | 2,3,3-Trichloro-propenyloxy | — | |
| 2.46 | $A_1$ | 2-Propynyloxy | — | |
| 2.47 | $A_1$ | 2-Butynyl-oxy | — | |
| 2.48 | $A_1$ | 3-Butynyl-oxy | — | |
| 2.49 | $A_1$ | 1-Methyl-2-propynyloxy | — | |
| 2.50 | $A_1$ | Cyclopropyl | — | |

TABLE 2-continued

Compounds of the formula II

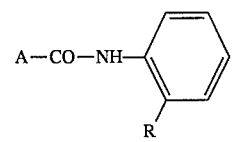

| No. | A | R | X | Phys. data mp [°C.] |
|---|---|---|---|---|
| 2.51 | $A_1$ | Cyclobutyl | — | |
| 2.52 | $A_1$ | Cyclopentyl | — | 112–113 |
| 2.53 | $A_1$ | Cyclohexyl | — | 120–121 |
| 2.54 | $A_1$ | 2-Cyclopentenyl | — | 128–129 |
| 2.55 | $A_1$ | 1-Cyclopentenyl | — | |
| 2.56 | $A_1$ | 2-Cyclohexenyl | — | 95–96 |
| 2.57 | $A_1$ | 1-Cyclohexenyl | — | |
| 2.58 | $A_1$ | Cyclopentyloxy | — | |
| 2.59 | $A_1$ | Cyclohexyloxy | — | |
| 2.60 | $A_1$ | 2-Cyclopentenyloxy | — | |
| 2.61 | $A_1$ | 2-Cyclohexenyloxy | — | oil |
| 2.62 | $A_2$ | $i\text{-}C_3H_7$ | $CH_2$ | 99–101 |
| 2.63 | $A_2$ | $n\text{-}C_3H_7$ | $CH_2$ | |
| 2.64 | $A_2$ | $n\text{-}C_4H_9$ | $CH_2$ | |
| 2.65 | $A_2$ | $sec.\text{-}C_4H_9$ | $CH_2$ | 81–82 |
| 2.66 | $A_2$ | $i\text{-}C_4H_9$ | $CH_2$ | 81–83 |
| 2.67 | $A_2$ | $tert.\text{-}C_4H_9$ | $CH_2$ | |
| 2.68 | $A_2$ | $n\text{-}C_5H_{11}$ | $CH_2$ | |
| 2.69 | $A_2$ | $sec.\text{-}C_5H_{11}$ | $CH_2$ | |
| 2.70 | $A_2$ | $n\text{-}C_6H_{13}$ | $CH_2$ | |
| 2.71 | $A_2$ | $n\text{-}C_7H_{15}$ | $CH_2$ | |
| 2.72 | $A_2$ | $sec.\text{-}C_7H_{15}$ | $CH_2$ | |
| 2.73 | $A_2$ | 1-Methylvinyl | $CH_2$ | |
| 2.74 | $A_2$ | 2-Methylvinyl | $CH_2$ | |
| 2.75 | $A_2$ | Allyl | $CH_2$ | |
| 2.76 | $A_2$ | 2-Methylallyl | $CH_2$ | |
| 2.77 | $A_2$ | 2-Ethylallyl | $CH_2$ | |
| 2.78 | $A_2$ | 1-Methylallyl | $CH_2$ | |
| 2.79 | $A_2$ | 1-Ethylallyl | $CH_2$ | |
| 2.80 | $A_2$ | 1-Methyl-2-butenyl | $CH_2$ | |
| 2.81 | $A_2$ | 1-Ethyl-2-butenyl | $CH_2$ | |
| 2.82 | $A_2$ | 1-Isopropyl-2-butenyl | $CH_2$ | |
| 2.83 | $A_2$ | 1-n-Butyl-2-butenyl | $CH_2$ | |
| 2.84 | $A_2$ | 1-Methyl-2-pentenyl | $CH_2$ | |
| 2.85 | $A_2$ | 1,4-Dimethyl-2-pentenyl | $CH_2$ | |
| 2.86 | $A_2$ | Propargyl | $CH_2$ | |
| 2.87 | $A_2$ | 2-Butynyl | $CH_2$ | |
| 2.88 | $A_2$ | 3-Butynyl | $CH_2$ | |
| 2.89 | $A_2$ | Ethoxy | $CH_2$ | |
| 2.90 | $A_2$ | Propoxy | $CH_2$ | |
| 2.91 | $A_2$ | 1-Methylethoxy | $CH_2$ | |
| 2.92 | $A_2$ | n-Butoxy | $CH_2$ | |
| 2.93 | $A_2$ | 1-Methylpropoxy | $CH_2$ | |
| 2.94 | $A_2$ | 2-Methylpropoxy | $CH_2$ | |
| 2.95 | $A_2$ | 1,1-Dimethylethoxy | $CH_2$ | |
| 2.96 | $A_2$ | n-Pentyloxy | $CH_2$ | |
| 2.97 | $A_2$ | n-Hexyloxy | $CH_2$ | |
| 2.98 | $A_2$ | 2-Ethylhexyloxy | $CH_2$ | |
| 2.99 | $A_2$ | 2-Propenyloxy | $CH_2$ | |
| 2.100 | $A_2$ | 2-Butentyloxy | $CH_2$ | |
| 2.101 | $A_2$ | 1-Methyl-2-propenyloxy | $CH_2$ | 67–69 |
| 2.102 | $A_2$ | 2-Pentenyloxy | $CH_2$ | |
| 2.103 | $A_2$ | 3-Pentenyloxy | $CH_2$ | |
| 2.104 | $A_2$ | 3-chloro-2-propenyloxy | $CH_2$ | |
| 2.105 | $A_2$ | 2,3-Dichloro-2-propenyloxy | $CH_2$ | |
| 2.106 | $A_2$ | 2,3,3-Trichloro-propenyloxy | $CH_2$ | |
| 2.107 | $A_2$ | 2-Propynyloxy | $CH_2$ | |
| 2.108 | $A_2$ | 2-Butynyl-oxy | $CH_2$ | |
| 2.109 | $A_2$ | 3-Butynyl-oxy | $CH_2$ | |
| 2.110 | $A_2$ | 1-Methyl-2-propynyloxy | $CH_2$ | |
| 2.111 | $A_2$ | Cyclopropyl | $CH_2$ | |
| 2.112 | $A_2$ | Cyclobutyl | $CH_2$ | |
| 2.113 | $A_2$ | Cyclopentyl | $CH_2$ | 109–111 |
| 2.114 | $A_2$ | Cyclohexyl | $CH_2$ | 118–123 |
| 2.115 | $A_2$ | 2-Cyclopentenyl | $CH_2$ | 87–89 |

TABLE 2-continued

Compounds of the formula II

A—CO—NH—⌬—R (ortho)

| No. | A | R | X | Phys. data mp [°C.] |
|---|---|---|---|---|
| 2.116 | A₂ | 1-Cyclopentenyl | CH₂ | |
| 2.117 | A₂ | 2-Cyclohexenyl | CH₂ | 85–87 |
| 2.118 | A₂ | 1-Cyclohexenyl | CH₂ | |
| 2.119 | A₂ | Cyclopentyloxy | CH₂ | 60–91 |
| 2.120 | A₂ | Cyclohexyloxy | CH₂ | |
| 2.121 | A₂ | 2-Cyclopentenyloxy | CH₂ | |
| 2.122 | A₂ | 2-Cyclohexenyloxy | CH₂ | oil |
| 2.123 | A₂ | i-C₃H₇ | S | |
| 2.124 | A₂ | n-C₃H₇ | S | |
| 2.125 | A₂ | n-C₄H₉ | S | |
| 2.126 | A₂ | sec.-C₄H₉ | S | oil |
| 2.127 | A₂ | i-C₄H₉ | S | oil |
| 2.128 | A₂ | tert.-C₄H₉ | S | |
| 2.129 | A₂ | n-C₅H₁₁ | S | |
| 2.130 | A₂ | sec.-C₅H₁₁ | S | |
| 2.131 | A₂ | n-C₆H₁₃ | S | |
| 2.132 | A₂ | n-C₇H₁₅ | S | |
| 2.133 | A₂ | sec.-C₇H₁₅ | S | |
| 2.134 | A₂ | 1-Methylvinyl | S | |
| 2.135 | A₂ | 2-Methylvinyl | S | |
| 2.136 | A₂ | Allyl | S | |
| 2.137 | A₂ | 2-Methylallyl | S | |
| 2.138 | A₂ | 2-Ethylallyl | S | |
| 2.139 | A₂ | 1-Methylallyl | S | |
| 2.140 | A₂ | 1-Ethylallyl | S | |
| 2.141 | A₂ | 1-Methyl-2-butenyl | S | |
| 2.142 | A₂ | 1-Ethyl-2-butenyl | S | |
| 2.143 | A₂ | 1-Isopropyl-2-butenyl | S | |
| 2.144 | A₂ | 1-n-Butyl-2-butenyl | S | |
| 2.145 | A₂ | 1-Methyl-2-pentenyl | S | |
| 2.146 | A₂ | 1,4-Dimethyl-2-pentenyl | S | |
| 2.147 | A₂ | Propargyl | S | |
| 2.148 | A₂ | 2-Butynyl | S | |
| 2.149 | A₂ | 3-Butynyl | S | |
| 2.150 | A₂ | Ethoxy | S | |
| 2.151 | A₂ | Propoxy | S | |
| 2.152 | A₂ | 1-Methylethoxy | S | |
| 2.153 | A₂ | n-Butoxy | S | |
| 2.154 | A₂ | 1-Methylpropoxy | S | oil |
| 2.155 | A₂ | 2-Methylpropoxy | S | |
| 2.156 | A₂ | 1,1-Dimethylethoxy | S | |
| 2.157 | A₂ | n-Pentyloxy | S | |
| 2.158 | A₂ | n-Hexyloxy | S | |
| 2.159 | A₂ | 2-Ethylhexyloxy | S | |
| 2.160 | A₂ | 2-Propenyloxy | S | |
| 2.161 | A₂ | 2-Butenyloxy | S | |
| 2.162 | A₂ | 1-Methyl-2-propenyloxy | S | 65–67 |
| 2.163 | A₂ | 2-Pentenyloxy | S | |
| 2.164 | A₂ | 3-Pentenyloxy | S | |
| 2.165 | A₂ | 3-chloro-2-propenyloxy | S | |
| 2.166 | A₂ | 2,3-Dichloro-2-propenyloxy | S | |
| 2.167 | A₂ | 2,3,3-Trichloro-propenyloxy | S | |
| 2.168 | A₂ | 2-Propynyloxy | S | |
| 2.169 | A₂ | 2-Butynyl-oxy | S | |
| 2.170 | A₂ | 3-Butynyl-oxy | S | |
| 2.171 | A₂ | 1-Methyl-2-propynyloxy | S | |
| 2.172 | A₂ | Cyclopropyl | S | |
| 2.173 | A₂ | Cyclobutyl | S | |
| 2.174 | A₂ | Cyclopentyl | S | 62–64 |
| 2.175 | A₂ | Cyclohexyl | S | 120–122 |
| 2.176 | A₂ | 2-Cyclopentenyl | S | 76–78 |
| 2.177 | A₂ | 1-Cyclopentenyl | S | |
| 2.178 | A₂ | 2-Cyclohexenyl | S | 70–72 |
| 2.179 | A₂ | 1-Cyclohexenyl | S | |
| 2.180 | A₂ | Cyclopentyloxy | S | 88–90 |
| 2.181 | A₂ | Cyclohexyloxy | S | |
| 2.182 | A₂ | 2-Cyclopentenyloxy | S | |
| 2.183 | A₂ | 2-Cyclohexenyloxy | S | oil |
| 2.184 | A₁ | 1-Ethylpropoxy | — | 65–66 |
| 2.185 | A₁ | 3-Methyl-2-butenyloxy | — | oil |
| 2.186 | A₂ | 1-Ethylpropoxy | CH₂ | oil |
| 2.187 | A₂ | 1-Ethylpropoxy | S | oil |

Manufacturing examples

Example 5

At 0° C., 3.1 g of 2-methylbenzoic chloride is dripped into a solution of 3.0 g of sec-butyl-aniline and 2.0 g of triethylamine in 30 ml of tetrahydrofuran, and the mixture is stirred for 2 hours at 0° C. After dilution with 500 ml of water, extraction with ethyl acetate and evaporation of the solvent, there is isolated 2-methylbenzoic acid-2-sec-butylanilide; m.p. 89°–90° C. (Compound No. 2.4).

Example 6

At 0° C., 2.5 g thionyl chloride is dripped into a solution of 3.0 g of 2-methyl-5,6-dihydropyran-3-carboxylic acid. After the mixture has been stirred for 1 hour, 2.8 g of 2-isopropylaniline is added and the whole is stirred for 12 hours at room temperature (20° C.). The pyridine is evaporated off, 50 ml of water is stirred in, the pH is adjusted to 3 with dilute hydrochloric acid, and extraction is carried out with ethyl acetate. The solvent is evaporated, the residue is mixed with diisopropyl ether, and there is isolated 3.3 g of 2-methyl-5,6-dihydropyran-3-carboxylic acid-2-isopropylanilide; m.p.: 99°–101° C. (Compound No. 2.62).

The invention further relates to the use of 2-aminobiphenyl derivatives of the general formula II

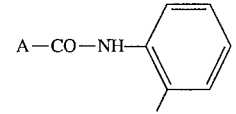

where the substituents have the following meanings:

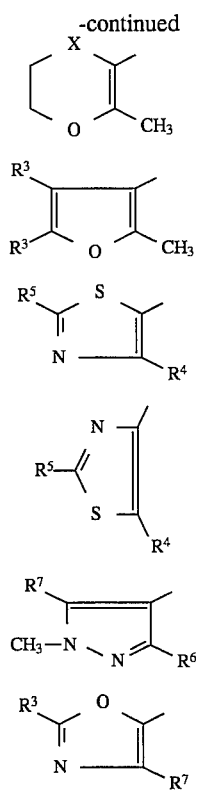

X methylene, sulfur, sulfinyl, sulfonyl (SO$_2$),
R$^1$ methyl, trifluoromethyl, chlorine, bromine, iodine,
R$^2$ trifluoromethyl, chlorine,
R$^3$ hydrogen or methyl
R$^4$ methyl, trifluoromethyl, chlorine
R$^5$ hydrogen, methyl, chlorine
R$^6$ methyl, trifluoromethyl
R$^7$ methyl, chlorine
R$^8$ C$_1$–C$_4$-alkyl, C$_1$–C$_4$-alkoxy, C$_1$–C$_4$-alkylthio, halogen for combating Botrytis.

The compounds of the formula III are obtained for instance by reacting a correspondingly substituted carboxylic halide of the formula 4

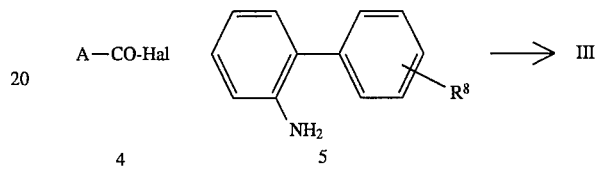

Hal denoting chlorine or bromine, with an ortho-substituted aniline of the formula 5 in the presence of a base. The carboxylic acids and their halides of the formula 4 are known. Some of the anilines of the formula 5 are known or can be prepared by known processes (Tetrahedron Letters, Vol. 28 p. 5093 (1987); THL Vol 295463 (1988)).

TABLE 3

| No. | A | R$^1$ | R$^2$ | R$^3$ | R$^4$ | R$^5$ | R$^6$ | R$^7$ | R$^8$ | X | Phys. data [°C.] |
|---|---|---|---|---|---|---|---|---|---|---|---|
| 3.1 | A$_1$ | CH$_3$ | — | — | — | — | — | — | 2-F | — | |
| 3.2 | A$_1$ | CH$_3$ | — | — | — | — | — | — | 4-F | — | |
| 3.3 | A$_1$ | CF$_3$ | — | — | — | — | — | — | 2-F | — | |
| 3.4 | A$_1$ | CF$_3$ | — | — | — | — | — | — | 4-F | — | |
| 3.5 | A$_2$ | — | Cl | — | — | — | — | — | 2-F | — | |
| 3.6 | A$^2$ | — | Cl | — | — | — | — | — | 2-CH$_3$ | — | 71–73 |
| 3.7 | A$_2$ | — | Cl | — | — | — | — | — | 2-Cl | — | |
| 3.8 | A$_2$ | — | Cl | — | — | — | — | — | 2-OCH$_3$ | — | |
| 3.9 | A$_2$ | — | Cl | — | — | — | — | — | 3-F | — | |
| 3.10 | A$_2$ | — | Cl | — | — | — | — | — | 3-Cl | — | 95–98 |
| 3.11 | A$_2$ | — | Cl | — | — | — | — | — | 3-CH$_3$ | — | |
| 3.12 | A$_2$ | — | Cl | — | — | — | — | — | 3-OCH$_3$ | — | |
| 3.13 | A$_2$ | — | Cl | — | — | — | — | — | 3-OiC$_3$H$_7$ | — | |
| 3.14 | A$_2$ | — | Cl | — | — | — | — | — | 3-Br | — | |
| 3.15 | A$_2$ | — | Cl | — | — | — | — | — | 4-F | — | 156–157 |
| 3.16 | A$_2$ | — | Cl | — | — | — | — | — | 4-Cl | — | |
| 3.17 | A$_2$ | — | Cl | — | — | — | — | — | 4-CH$_3$ | — | |
| 3.18 | A$_2$ | — | Cl | — | — | — | — | — | 4-OCH$_3$ | — | |
| 3.19 | A$_2$ | — | Cl | — | — | — | — | — | 4-SCH$_3$ | — | |
| 3.20 | A$_3$ | — | — | — | — | — | — | — | 2-F | CH$_2$ | |
| 3.21 | A$_3$ | — | — | — | — | — | — | — | 3-F | CH$_2$ | |
| 3.22 | A$_3$ | — | — | — | — | — | — | — | 4-F | CH$_2$ | |
| 3.23 | A$_3$ | — | — | — | — | — | — | — | 3-Cl | CH$_2$ | |
| 3.24 | A$_3$ | — | — | — | — | — | — | — | 3-CH$_3$ | CH$_2$ | |
| 3.25 | A$_3$ | — | — | — | — | — | — | — | 2-F | S | |
| 3.26 | A$_3$ | — | — | — | — | — | — | — | 3-F | S | |
| 3.27 | A$_3$ | — | — | — | — | — | — | — | 4-F | S | |
| 3.28 | A$_3$ | — | — | — | — | — | — | — | 3-Cl | S | |
| 3.29 | A$_3$ | — | — | — | — | — | — | — | 3-CH$_3$ | S | |
| 3.30 | A$_3$ | — | — | — | — | — | — | — | 2-F | SO$_2$ | |
| 3.31 | A$_3$ | — | — | — | — | — | — | — | 3-F | SO$_2$ | |
| 3.32 | A$_3$ | — | — | — | — | — | — | — | 4-F | SO$_2$ | |
| 3.33 | A$_3$ | — | — | — | — | — | — | — | 3-Cl | SO$_2$ | |
| 3.34 | A$_3$ | — | — | — | — | — | — | — | 3-CH$_3$ | SO$_2$ | |
| 3.35 | A$_5$ | — | — | — | CF$_3$ | CH$_3$ | — | — | 2-F | — | |

TABLE 3-continued

| No. | A | R¹ | R² | R³ | R⁴ | R⁵ | R⁶ | R⁷ | R⁸ | X | Phys. data [°C.] |
|---|---|---|---|---|---|---|---|---|---|---|---|
| 3.36 | A₅ | — | — | — | CF₃ | CH₃ | — | — | 3-F | — | |
| 3.37 | A₅ | — | — | — | CF₃ | CH₃ | — | — | 4-F | — | |
| 3.38 | A₇ | — | — | — | — | — | CH₃ | Cl | 2-F | — | |
| 3.39 | A₇ | — | — | — | — | — | CH₃ | Cl | 3-F | — | |
| 3.40 | A₇ | — | — | — | — | — | CH₃ | Cl | 4-F | — | |
| 3.41 | A₇ | — | — | — | — | — | CF₃ | Cl | 2-F | — | |
| 3.42 | A₇ | — | — | — | — | — | CF₃ | Cl | 4-F | — | |

The invention further relates to the use of 2-aminobiphenyl derivatives of the general formula IV

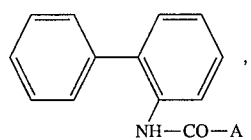   IV where the substituents have the following meanings:

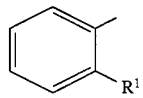   (A1)

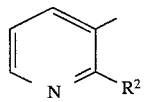   (A2)

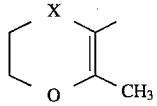   (A3)

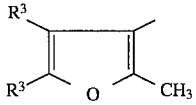   (A4)

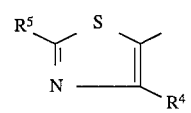   (A5)

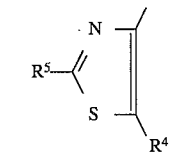   (A6)

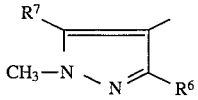   (A7)

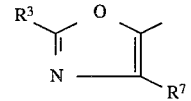   (A8)

X methylene, sulfinyl, sulfonyl (SO₂),

R¹ methyl, trifluoromethyl, chlorine, bromine, iodine,

R² trifluoromethyl, chlorine

R³ hydrogen or methyl

R⁴ methyl, trifluoromethyl, chlorine

R⁵ hydrogen, methyl, chlorine

R⁶ methyl, trifluoromethyl

R⁷ methyl, chlorine, for combating Botrytis.

The compounds of the formula IV are obtained for example by reacting a corresponding aromatic or heterocyclic acid halide 4 with 2-aminobiphenyl 6 in the presence of a base.

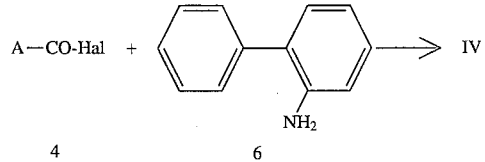 → IV 4    6

Hal is chlorine or bromine.

The acids of the formula A-CO₂H and their halides II are known.

TABLE 4

| No. | A | R¹ | R² | R³ | R⁴ | R⁵ | R⁶ | R⁷ | X | Phys. data [°C.] |
|---|---|---|---|---|---|---|---|---|---|---|
| 4.1 | A₁ | CH₃ | — | — | — | — | — | — | — | 87–88 |
| 4.2 | A₁ | Br | — | — | — | — | — | — | — | 113–115 |
| 4.3 | A₂ | — | Cl | — | — | — | — | — | — | 151–152 |
| 4.4 | A₃ | — | — | — | — | — | — | — | CH₂ | 76–77 |
| 4.5 | A₄ | — | — | CH₃ | — | — | — | — | — | 104–106 |
| 4.6 | A₅ | — | — | — | CH₃ | CH₃ | — | — | — | 136–137 |

TABLE 5

| No. | A | R¹ | R² | R³ | R⁴ | R⁵ | R⁶ | R⁷ | X | Phys. data [°C.] |
|---|---|---|---|---|---|---|---|---|---|---|
| 5.1 | $A_1$ | $CF_3$ | — | — | — | — | — | — | — | 138–139 |
| 5.2 | $A_1$ | J | — | — | — | — | — | — | — | 129–132 |
| 5.3 | $A_1$ | — | $CF_3$ | — | — | — | — | — | — | |
| 5.4 | $A_2$ | — | — | — | — | — | — | — | SO | |
| 5.5 | $A_3$ | — | — | — | — | — | — | — | $SO_2$ | |
| 5.6 | $A_5$ | — | — | — | $CF_3$ | $CH_3$ | — | — | — | 116–118 |
| 5.7 | $A_6$ | — | — | — | $CH_3$ | $CH_3$ | — | — | — | |
| 5.8 | $A_6$ | — | — | — | Cl | Cl | — | — | — | |
| 5.9 | $A_7$ | — | — | — | — | — | $CH_3$ | Cl | — | 108–109 |
| 5.10 | $A_7$ | — | — | — | — | — | $CF_3$ | Cl | — | |
| 5.11 | $A_7$ | — | — | — | — | — | $CH_3$ | $CH_3$ | — | |
| 5.11 | $A_1$ | Cl | — | — | — | — | — | — | — | 100–103 |

The invention further relates to the use of carboxanilide derivatives of the general formula V

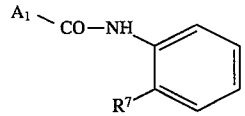

where the substituents have the following meanings:

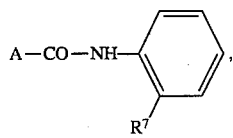 (A1)

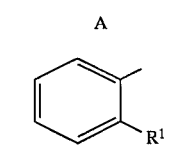 (A2)

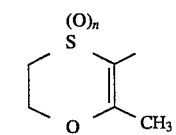 (A3)

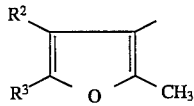 (A4)

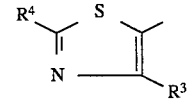 (A5)

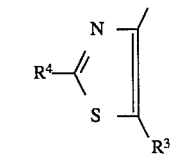 (A6)

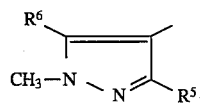 (A7)

n 1 or 2

R¹ trifluoromethyl, chlorine, bromine, iodine,

R² hydrogen or methyl

R³ methyl, trifluoromethyl, chlorine

R⁴ hydrogen, methyl, chlorine,

R⁵ methyl, trifluoromethyl

R⁶ methyl, chlorine

R⁷ unsubstituted or halogen-substituted $C_3$–$C_{12}$-alkyl, unsubstituted or halogen-substituted $C_3$–$C_{12}$-alkenyl, $C_3$–$C_6$-alkynyl, unsubstituted or halogen-substituted $C_2$–$C_{12}$-alkoxy, unsubstituted or halogen-substituted $C_3$–$C_{12}$-alkenyloxy, $C_3$–$C_{12}$-alkynyloxy, unsubstituted or $C_1$–$C_4$-alkyl-substituted $C_3$–$C_6$-cycloalkyl, unsubstituted or $C_1$–$C_4$-alkyl-substituted $C_4$–$C_6$-cycloalkenyl, unsubstituted or $C_1$–$C_4$-alkyl-substituted $C_5$–$C_6$-cycloalkyloxy, unsubstituted or $C_1$–$C_4$-alkyl-substituted $C_5$–$C_6$-cycloalkenyloxy for combating Botrytis.

TABLE 6

Compounds of the formula I where A is $A_1$

| No. | R¹ | R⁷ | Phys. data mp [°C.] |
|---|---|---|---|
| 6.1 | $CF_3$ | i-$C_3H_7$ | 160–162 |
| 6.2 | $CF_3$ | n-$C_3H_7$ | 151–152 |
| 6.3 | $CF_3$ | n-$C_4H_9$ | |
| 6.4 | $CF_3$ | sec.-$C_4H_9$ | 83–84 |
| 6.5 | $CF_3$ | i-$C_4H_9$ | 133–135 |
| 6.6 | $CF_3$ | tert.-$C_4H_9$ | |
| 6.7 | $CF_3$ | n-$C_5H_{11}$ | |
| 6.8 | $CF_3$ | sec.-$C_5H_{11}$ | |
| 6.9 | $CF_3$ | n-$C_6H_{13}$ | |
| 6.10 | $CF_3$ | n-$C_7H_{15}$ | |
| 6.11 | $CF_3$ | sec.-$C_7H_{15}$ | |
| 6.12 | $CF_3$ | 1-Methylvinyl | |
| 6.13 | $CF_3$ | 2-Methylvinyl | |
| 6.14 | $CF_3$ | Allyl | |
| 6.15 | $CF_3$ | 2-Methylallyl | |
| 6.16 | $CF_3$ | 2-Ethylallyl | |
| 6.17 | $CF_3$ | 1-Methylallyl | |
| 6.18 | $CF_3$ | 1-Ethylallyl | |
| 6.19 | $CF_3$ | 1-Methyl-2-butenyl | |
| 6.20 | $CF_3$ | 1-Ethyl-2-butenyl | |
| 6.21 | $CF_3$ | 1-Isopropyl-2-butenyl | |
| 6.22 | $CF_3$ | 1-n-Butyl-2-butenyl | |
| 6.23 | $CF_3$ | 1-Methyl-2-pentenyl | |
| 6.24 | $CF_3$ | 1,4-Dimethyl-2-pentenyl | |
| 6.25 | $CF_3$ | Propargyl | |
| 6.26 | $CF_3$ | 2-butynyl | |
| 6.27 | $CF_3$ | 3-butynyl | |

TABLE 6-continued

Compounds of the formula I where A is $A_1$

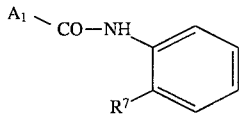

| No. | $R^1$ | $R^7$ | Phys. data mp [°C.] |
|---|---|---|---|
| 6.28 | $CF_3$ | Ethoxy | |
| 6.29 | $CF_3$ | Propoxy | |
| 6.30 | $CF_3$ | 1-Methylethoxy | |
| 6.31 | $CF_3$ | n-Butoxy | |
| 6.32 | $CF_3$ | 1-Methylpropoxy | |
| 6.33 | $CF_3$ | 2-Methylpropoxy | |
| 6.34 | $CF_3$ | 1,1-Dimethylethoxy | |
| 6.35 | $CF_3$ | n-Pentyloxy | |
| 6.36 | $CF_3$ | n-Hexyloxy | |
| 6.37 | $CF_3$ | 2-Ethylhexyloxy | |
| 6.38 | $CF_3$ | 2-Propenyloxy | |
| 6.39 | $CF_3$ | 2-Butentyloxy | |
| 6.40 | $CF_3$ | 2-Methyl-2-propenyloxy | |
| 6.41 | $CF_3$ | 2-Pentenyloxy | |
| 6.42 | $CF_3$ | 3-Pentenyloxy | |
| 6.43 | $CF_3$ | 3-chloro-2-propenyloxy | |
| 6.44 | $CF_3$ | 2,3-Dichloro-2-propenyloxy | |
| 6.45 | $CF_3$ | 2,3,3-Trichloro-propenyloxy | |
| 6.46 | $CF_3$ | 2-propynyloxy | |
| 6.47 | $CF_3$ | 2-butynyl-oxy | |
| 6.48 | $CF_3$ | 3-butynyl-oxy | |
| 6.49 | $CF_3$ | 1-Methyl-2-propynyloxy | |
| 6.50 | $CF_3$ | Cyclopropyl | |
| 6.51 | $CF_3$ | Cyclobutyl | |
| 6.52 | $CF_3$ | Cyclopentyl | 150–152 |
| 6.53 | $CF_3$ | Cyclohexyl | 130–132 |
| 6.54 | $CF_3$ | 2-Cyclopentenyl | 160–161 |
| 6.55 | $CF_3$ | 1-Cyclopentenyl | |
| 6.56 | $CF_3$ | 2-Cyclohexenyl | 103–105 |
| 6.57 | $CF_3$ | 1-Cyclohexenyl | |
| 6.58 | $CF_3$ | Cyclopentyloxy | |
| 6.59 | $CF_3$ | Cyclohexyloxy | |
| 6.60 | $CF_3$ | 2-Cyclopentenyloxy | |
| 6.61 | $CF_3$ | 2-Cyclohexenyloxy | |

TABLE 7

Compounds of the formula V where A is $A_1$

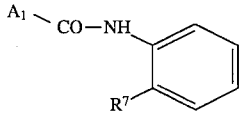

| No. | $R^1$ | $R^7$ | Phys. data mp [°C.] |
|---|---|---|---|
| 7.1 | Cl | i-$C_3H_7$ | 125–127 |
| 7.2 | Cl | n-$C_3H_7$ | 108–110 |
| 7.3 | Cl | n-$C_4H_9$ | |
| 7.4 | Cl | sec.-$C_4H_9$ | 73–74 |
| 7.5 | Cl | i-$C_4H_9$ | 90–92 |
| 7.6 | Cl | tert.-$C_4H_9$ | |
| 7.7 | Cl | n-$C_5H_{11}$ | |
| 7.8 | Cl | sec.-$C_5H_{11}$ | |
| 7.9 | Cl | n-$C_6H_{13}$ | |
| 7.10 | Cl | n-$C_7H_{15}$ | |
| 7.11 | Cl | sec.-$C_7H_{15}$ | |
| 7.12 | Cl | 1-Methylvinyl | |
| 7.13 | Cl | 2-Methylvinyl | |
| 7.14 | Cl | Allyl | |
| 7.15 | Cl | 2-Methylally | |
| 7.16 | Cl | 2-Ethylallyl | |

TABLE 7-continued

Compounds of the formula V where A is $A_1$

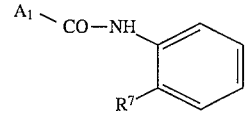

| No. | $R^1$ | $R^7$ | Phys. data mp [°C.] |
|---|---|---|---|
| 7.17 | Cl | 1-Methylallyl | |
| 7.18 | Cl | 1-Ethylallyl | |
| 7.19 | Cl | 1-Methyl-2-butenyl | |
| 7.20 | Cl | 1-Ethyl-2-butenyl | |
| 7.21 | Cl | 1-Isopropyl-2-butenyl | |
| 7.22 | Cl | 1-n-Butyl-2-butenyl | |
| 7.23 | Cl | 1-Methyl-2-pentenyl | |
| 7.24 | Cl | 1,4-Dimethyl-2-pentenyl | |
| 7.25 | Cl | Propargyl | |
| 7.26 | Cl | 2-butynyl | |
| 7.27 | Cl | 3-butynyl | |
| 7.28 | Cl | Ethoxy | |
| 7.29 | Cl | Propoxy | |
| 7.30 | Cl | 1-Methylethoxy | |
| 7.31 | Cl | n-Butoxy | |
| 7.32 | Cl | 1-Methylpropoxy | |
| 7.33 | Cl | 2-Methylpropoxy | |
| 7.34 | Cl | 1,1-Dimethylethoxy | |
| 7.35 | Cl | n-Pentyloxy | |
| 7.36 | Cl | n-Hexyloxy | |
| 7.37 | Cl | 2-Ethylhexyloxy | |
| 7.38 | Cl | 2-Propenyloxy | |
| 7.39 | Cl | 2-Butentyloxy | |
| 7.40 | Cl | 2-Methyl-2-propenyloxy | |
| 7.41 | Cl | 2-Pentenyloxy | |
| 7.42 | Cl | 3-Pentenyloxy | |
| 7.43 | Cl | 3-chloro-2-propenyloxy | |
| 7.44 | Cl | 2,3-Dichloro-2-propenyloxy | |
| 7.45 | Cl | 2,3,3-Trichloro-propenyloxy | |
| 7.46 | Cl | 2-propynyloxy | |
| 7.47 | Cl | 2-butynyl-oxy | |
| 7.48 | Cl | 3-butynyl-oxy | |
| 7.49 | Cl | 1-Methyl-2-propynyloxy | |
| 7.50 | Cl | Cyclopropyl | |
| 7.51 | Cl | Cyclobutyl | |
| 7.52 | Cl | Cyclopentyl | 110–111 |
| 7.53 | Cl | Cyclohexyl | 141–142 |
| 7.54 | Cl | 2-Cyclopentenyl | 110–112 |
| 7.55 | Cl | 1-Cyclopentenyl | |
| 7.56 | Cl | 2-Cyclohexenyl | 84–86 |
| 7.57 | Cl | 1-Cyclohexenyl | |
| 7.58 | Cl | Cyclopentyloxy | |
| 7.59 | Cl | Cyclohexyloxy | |
| 7.60 | Cl | 2-Cyclopentenyloxy | |
| 7.61 | Cl | 2-Cyclohexenyloxy | |

TABLE 8

Compounds of the formula V where A is $A_2$

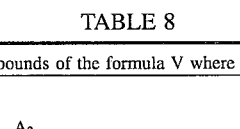

| No. | n | $R^7$ | Phys. data mp [°C.] |
|---|---|---|---|
| 8.1 | 2 | i-$C_3H_7$ | |
| 8.2 | 2 | n-$C_3H_7$ | |
| 8.3 | 2 | n-$C_4H_9$ | |
| 8.4 | 2 | sec.-$C_4H_9$ | 96–98 |
| 8.5 | 2 | i-$C_4H_9$ | 85–86 |

TABLE 8-continued

Compounds of the formula V where A is A₂

$$A_2-CO-NH-\underset{R^7}{C_6H_4}$$

| No. | n | R⁷ | Phys. data mp [°C.] |
|---|---|---|---|
| 8.6 | 2 | tert.-C₄H₉ | |
| 8.7 | 2 | n-C₅H₁₁ | |
| 8.8 | 2 | sec.-C₅H₁₁ | |
| 8.9 | 2 | n-C₆H₁₃ | |
| 8.10 | 2 | n-C₇H₁₅ | |
| 8.11 | 2 | sec.-C₇H₁₅ | |
| 8.12 | 2 | 1-Methylvinyl | |
| 8.13 | 2 | 2-Methylvinyl | |
| 8.14 | 2 | Allyl | |
| 8.15 | 2 | 2-Methylallyl | |
| 8.16 | 2 | 2-Ethylallyl | |
| 8.17 | 2 | 1-Methylallyl | |
| 8.18 | 2 | 1-Ethylallyl | |
| 8.19 | 2 | 1-Methyl-2-butenyl | |
| 8.20 | 2 | 1-Ethyl-2-butenyl | |
| 8.21 | 2 | 1-Isopropyl-2-butenyl | |
| 8.22 | 2 | 1-n-Butyl-2-butenyl | |
| 8.23 | 2 | 1-Methyl-2-pentenyl | |
| 8.24 | 2 | 1,4-Dimethyl-2-pentenyl | |
| 8.25 | 2 | Propargyl | |
| 8.26 | 2 | 2-butynyl | |
| 8.27 | 2 | 3-butynyl | |
| 8.28 | 2 | Ethoxy | |
| 8.29 | 2 | Propoxy | |
| 8.30 | 2 | 1-Methylethoxy | |
| 8.31 | 2 | n-Butoxy | |
| 8.32 | 2 | 1-Methylpropoxy | 100–102 |
| 8.33 | 2 | 2-Methylpropoxy | |
| 8.34 | 2 | 1,1-Dimethylethoxy | |
| 8.35 | 2 | n-Pentyloxy | |
| 8.36 | 2 | n-Hexyloxy | |
| 8.37 | 2 | 2-Ethylhexyloxy | |
| 8.38 | 2 | 2-Propenyloxy | |
| 8.39 | 2 | 2-Butentyloxy | |
| 8.40 | 2 | 2-methyl-2-propenyloxy | |
| 8.41 | 2 | 2-Pentenyloxy | |
| 8.42 | 2 | 3-Pentenyloxy | |
| 8.43 | 2 | 3-chloro-2-propenyloxy | |
| 8.44 | 2 | 2,3-Dichloro-2-propenyloxy | |
| 8.45 | 2 | 2,3,3-Trichloro-propenyloxy | |
| 8.46 | 2 | 2-propynyloxy | |
| 8.47 | 2 | 2-butynyl-oxy | |
| 8.48 | 2 | 3-butynyl-oxy | |
| 8.49 | 2 | 1-Methyl-2-propynyloxy | |
| 8.50 | 2 | Cyclopropyl | |
| 8.51 | 2 | Cyclobutyl | |
| 8.52 | 2 | Cyclopentyl | 128–130 |
| 8.53 | 2 | Cyclohexyl | 134–135 |
| 8.54 | 2 | 2-Cyclopentenyl | |
| 8.55 | 2 | 1-Cyclopentenyl | |
| 8.56 | 2 | 2-Cyclohexenyl | |
| 8.57 | 2 | 1-Cyclohexenyl | |
| 8.58 | 2 | Cyclopentyloxy | |
| 8.59 | 2 | Cyclohexyloxy | |
| 8.60 | 2 | 2-Cyclopentenyloxy | |
| 8.61 | 2 | 2-Cyclohexenyloxy | |
| 8.62 | 1 | i-C₃H₇ | |
| 8.63 | 1 | n-C₃H₇ | |
| 8.64 | 1 | n-C₄H₉ | |
| 8.65 | 1 | sec.-C₄H₉ | oil |
| 8.66 | 1 | i-C₄H₉ | oil |
| 8.67 | 1 | tert.-C₄H₉ | |
| 8.68 | 1 | n-C₅H₁₁ | |
| 8.69 | 1 | sec.-C₅H₁₁ | |
| 8.70 | 1 | n-C₆H₁₃ | |
| 8.71 | 1 | n-C₇H₁₅ | |
| 8.72 | 1 | sec.-C₇H₁₅ | |
| 8.73 | 1 | Ethoxy | |
| 8.74 | 1 | Propoxy | |
| 8.75 | 1 | 1-Methylethoxy | |
| 8.76 | 1 | n-Butoxy | |
| 8.77 | 1 | 1-Methylpropoxy | |
| 8.78 | 1 | 2-Methylpropoxy | |
| 8.79 | 1 | 1,1-Dimethylethoxy | |
| 8.80 | 1 | n-Pentyloxy | |
| 8.81 | 1 | n-Hexyloxy | |
| 8.82 | 1 | Cyclopentyl | |

TABLE 9

Compounds of the formula V where A is A₄

$$A_4-CO-NH-\underset{R^7}{C_6H_4}$$

| No. | R³ | R⁴ | R⁷ | Phys. data mp [°C.] |
|---|---|---|---|---|
| 9.1 | CF₃ | CH₃ | i-C₃H₇ | 115–116 |
| 9.2 | CF₃ | CH₃ | n-C₃H₇ | 114–116 |
| 9.3 | CF₃ | CH₃ | n-C₄H₉ | |
| 9.4 | CF₃ | CH₃ | sec.-C₄H₉ | 73–75 |
| 9.5 | CF₃ | CH₃ | i-C₄H₉ | 100–102 |
| 9.6 | CF₃ | CH₃ | tert.-C₄H₉ | |
| 9.7 | CF₃ | CH₃ | n-C₅H₁₁ | |
| 9.8 | CF₃ | CH₃ | sec.-C₅H₁₁ | |
| 9.9 | CF₃ | CH₃ | n-CH₆H₁ | |
| 9.10 | CF₃ | CH₃ | n-C₇H₁₅ | |
| 9.11 | CF₃ | CH₃ | sec.-C₇H₁₅ | |
| 9.12 | CF₃ | CH₃ | 1-Methylvinyl | |
| 9.13 | CF₃ | CH₃ | 2-Methylvinyl | |
| 9.14 | CF₃ | CH₃ | Allyl | |
| 9.15 | CF₃ | CH₃ | 2-Methylallyl | |
| 9.16 | CF₃ | CH₃ | 2-Ethylallyl | |
| 9.17 | CF₃ | CH₃ | 1-Methylallyl | |
| 9.18 | CF₃ | CH₃ | 1-Ethylallyl | |
| 9.19 | CF₃ | CH₃ | 1-Methyl-2-butenyl | |
| 9.20 | CF₃ | CH₃ | 1-Ethyl-2-butenyl | |
| 9.21 | CF₃ | CH₃ | 1-Isopropyl-2-butenyl | |
| 9.22 | CF₃ | CH₃ | 1-n-Butyl-2-butenyl | |
| 9.23 | CF₃ | CH₃ | 1-Methyl-2-pentenyl | |
| 9.24 | CF₃ | CH₃ | 1,4-Dimethyl-2-pentenyl | |
| 9.25 | CF₃ | CH₃ | Propargyl | |
| 9.26 | CF₃ | CH₃ | 2-butynyl | |
| 9.27 | CF₃ | CH₃ | 3-butynyl | |
| 9.28 | CF₃ | CH₃ | Ethoxy | |
| 9.29 | CF₃ | CH₃ | Propoxy | |
| 9.30 | CF₃ | CH₃ | 1-Methylethoxy | |
| 9.31 | CF₃ | CH₃ | n-Butoxy | |
| 9.32 | CF₃ | CH₃ | 1-Methylpropoxy | |
| 9.33 | CF₃ | CH₃ | 2-Methylpropoxy | |
| 9.34 | CF₃ | CH₃ | 1,1-Dimethylethoxy | |
| 9.35 | CF₃ | CH₃ | n-Pentyloxy | |
| 9.36 | CF₃ | CH₃ | n-Hexyloxy | |
| 9.37 | CF₃ | CH₃ | 2-Ethylhexyloxy | |
| 9.38 | CF₃ | CH₃ | 2-Propenyloxy | |
| 9.39 | CF₃ | CH₃ | 2-Butentyloxy | |

TABLE 9-continued

Compounds of the formula V where A is A₄

$$A_4\text{—CO—NH—}\underset{R^7}{\text{C}_6\text{H}_4}$$

| No. | R³ | R⁴ | R⁷ | Phys. data mp [°C.] |
|---|---|---|---|---|
| 9.40 | CF₃ | CH₃ | 2-Methyl-2-propenyloxy | |
| 9.41 | CF₃ | CH₃ | 2-Pentenyloxy | |
| 9.42 | CF₃ | CH₃ | 3-Pentenyloxy | |
| 9.43 | CF₃ | CH₃ | 3-chloro-2-propenyloxy | |
| 9.44 | CF₃ | CH₃ | 2,3-Dichloro-2-propenyloxy | |
| 9.45 | CF₃ | CH₃ | 2,3,3-Trichloro-propenyloxy | |
| 9.46 | CF₃ | CH₃ | 2-propynyloxy | |
| 9.47 | CF₃ | CH₃ | 2-butynyl-oxy | |
| 9.48 | CF₃ | CH₃ | 3-butynyl-oxy | |
| 9.49 | CF₃ | CH₃ | 1-Methyl-2-propynyloxy | |
| 9.50 | CF₃ | CH₃ | Cyclopropyl | |
| 9.51 | CF₃ | CH₃ | Cyclobutyl | |
| 9.52 | CF₃ | CH₃ | Cyclopentyl | 114–118 |
| 9.53 | CF₃ | CH₃ | Cyclohexyl | 100–104 |
| 9.54 | CF₃ | CH₃ | 2-Cyclopentenyl | 116–120 |
| 9.55 | CF₃ | CH₃ | 1-Cyclopentenyl | |
| 9.56 | CF₃ | CH₃ | 2-Cyclohexenyl | 96–98 |
| 9.57 | CF₃ | CH₃ | 1-Cyclohexenyl | |
| 9.58 | CF₃ | CH₃ | Cyclopentyloxy | |
| 9.59 | CF₃ | CH₃ | Cyclohexyloxy | |
| 9.60 | CF₃ | CH₃ | 2-Cyclopentenyloxy | |
| 9.61 | CF₃ | CH₃ | 2-Cyclohexenyloxy | |
| 9.62 | CH₃ | CH₃ | i-C₃H₇ | |
| 9.63 | CH₃ | CH₃ | n-C₃H₇ | |
| 9.64 | CH₃ | CH₃ | n-C₄H₉ | |
| 9.65 | CH₃ | CH₃ | sec.-C₄H₉ | 136 |
| 9.66 | CH₃ | CH₃ | i-C₄H₉ | 96–97 |
| 9.67 | CH₃ | CH₃ | tert.-C₄H₉ | |
| 9.68 | CH₃ | CH₃ | n-C₅H₁₁ | |
| 9.69 | CH₃ | CH₃ | sec.-C₅H₁₁ | |
| 9.70 | CH₃ | CH₃ | n-C₆H₁₃ | |
| 9.71 | CH₃ | CH₃ | n-C₇H₁₅ | |
| 9.72 | CH₃ | CH₃ | sec.-C₇H₁₅ | |
| 9.73 | CH₃ | CH₃ | Ethoxy | |
| 9.74 | CH₃ | CH₃ | Propoxy | |
| 9.75 | CH₃ | CH₃ | 1-Methylethoxy | |
| 9.76 | CH₃ | CH₃ | n-Butoxy | |
| 9.77 | CH₃ | CH₃ | 1-Methylpropoxy | |
| 9.78 | CH₃ | CH₃ | 2-Methylpropoxy | |
| 9.79 | CH₃ | CH₃ | 1,1-Dimethylethoxy | |
| 9.80 | CH₃ | CH₃ | n-Pentyloxy | |
| 9.81 | CH₃ | CH₃ | n-Hexyloxy | |
| 9.82 | CH₃ | CH₃ | Cyclopentyl | 128–130 |
| 9.83 | CH₃ | CH₃ | Cyclopentenyl | 128–129 |
| 9.84 | CH₃ | CH₃ | Cyclohexyl | 128–129 |
| 9.85 | CH₃ | CH₃ | 1-Ethyl-propoxy | 45–47 |
| 9.86 | CH₃ | CH₃ | Cyclopentyloxy | 97–99 |
| 9.87 | CH₃ | CH₃ | 2-Cyclohexenyloxy | 87–89 |
| 9.88 | CH₃ | CH₃ | 2-Methyl-2-propenyloxy | 103–105 |

TABLE 10

Compounds of the formula V where A is A₆

$$A_6\text{—CO—NH—}\underset{R^7}{\text{C}_6\text{H}_4}$$

| No. | R⁵ | R⁶ | R⁷ | Phys. data mp [°C.] |
|---|---|---|---|---|
| 10.1 | CH₃ | Cl | i-C₃H₇ | 108–110 |
| 10.2 | CH₃ | Cl | n-C₃H₇ | 129–130 |
| 10.3 | CH₃ | Cl | n-C₄H₉ | |
| 10.4 | CH₃ | Cl | sec.-C₄H₉ | 71–73 |
| 10.5 | CH₃ | Cl | i-C₄H₉ | 119–120 |
| 10.6 | CH₃ | Cl | tert-C₄H₉ | |
| 10.7 | CH₃ | Cl | n-C₅H₁₁ | |
| 10.8 | CH₃ | Cl | sec.-C₅H₁₁ | |
| 10.9 | CH₃ | Cl | n-C₆H₁₃ | |
| 10.10 | CH₃ | Cl | n-C₇H₁₅ | |
| 10.11 | CH₃ | Cl | sec.-C₇H₁₅ | |
| 10.12 | CH₃ | Cl | 1-Methylvinyl | |
| 10.13 | CH₃ | Cl | 2-Methylvinyl | |
| 10.14 | CH₃ | Cl | Allyl | |
| 10.15 | CH₃ | Cl | 2-Methylallyl | |
| 10.16 | CH₃ | Cl | 2-Ethylallyl | |
| 10.17 | CH₃ | Cl | 1-Methylallyl | |
| 10.18 | CH₃ | Cl | 1-Ethylallyl | |
| 10.19 | CH₃ | Cl | 1-Methyl-2-butenyl | |
| 10.20 | CH₃ | Cl | 1-Ethyl-2-butenyl | |
| 10.21 | CH₃ | Cl | 1-Isopropyl-2-butenyl | |
| 10.22 | CH₃ | Cl | 1-n-Butyl-2-butenyl | |
| 10.23 | CH₃ | Cl | 1-Methyl-2-pentenyl | |
| 10.24 | CH₃ | Cl | 1,4-Dimethyl-2-pentenyl | |
| 10.25 | CH₃ | Cl | Propargyl | |
| 10.26 | CH₃ | Cl | 2-butynyl | |
| 10.27 | CH₃ | Cl | 3-butynyl | |
| 10.28 | CH₃ | Cl | Ethoxy | |
| 10.29 | CH₃ | Cl | Propoxy | |
| 10.30 | CH₃ | Cl | 1-Methylethoxy | |
| 10.31 | CH₃ | Cl | n-Butoxy | |
| 10.32 | CH₃ | Cl | 1-Methylpropoxy | |
| 10.33 | CH₃ | Cl | 2-Methylpropoxy | |
| 10.34 | CH₃ | Cl | 1,1-Dimethylethoxy | |
| 10.35 | CH₃ | Cl | n-Pentyloxy | |
| 10.36 | CH₃ | Cl | n-Hexyloxy | |
| 10.37 | CH₃ | Cl | 2-Ethylhexyloxy | |
| 10.38 | CH₃ | Cl | 2-Propenyloxy | |
| 10.39 | CH₃ | Cl | 2-Butenyloxy | |
| 10.40 | CH₃ | Cl | 2-methyl-2-propenyloxy | |
| 10.41 | CH₃ | Cl | 2-Pentenyloxy | |
| 10.42 | CH₃ | Cl | 3-Pentenyloxy | |
| 10.43 | CH₃ | Cl | 3-chloro-2-propenyloxy | |
| 10.44 | CH₃ | Cl | 2,3-Dichloro-2-propenyloxy | |
| 10.45 | CH₃ | Cl | 2,3,3-Trichloro-propenyloxy | |
| 10.46 | CH₃ | Cl | 2-propynyloxy | |
| 10.47 | CH₃ | Cl | 2-butynyl-oxy | |
| 10.48 | CH₃ | Cl | 3-butynyl-oxy | |
| 10.49 | CH₃ | Cl | 1-Methyl-2-propynyloxy | |
| 10.50 | CH₃ | Cl | Cyclopropyl | |
| 10.51 | CH₃ | Cl | Cyclobutyl | |
| 10.52 | CH₃ | Cl | Cyclopentyl | 122–123 |
| 10.53 | CH₃ | Cl | Cyclohexyl | 143–144 |
| 10.54 | CH₃ | Cl | 2-Cyclopentenyl | 123–125 |
| 10.55 | CH₃ | Cl | 1-Cyclopentenyl | |
| 10.56 | CH₃ | Cl | 2-Cyclohexenyl | 114–116 |
| 10.57 | CH₃ | Cl | 1-Cyclohexenyl | |
| 10.58 | CH₃ | Cl | Cyclopentyloxy | |
| 10.59 | CH₃ | Cl | Cyclohexyloxy | |
| 10.60 | CH₃ | Cl | 2-Cyclopentenyloxy | |
| 10.61 | CH₃ | Cl | 2-Cyclohexenyloxy | |
| 10.62 | CF₃ | Cl | i-C₃H₇ | |
| 10.63 | CF₃ | Cl | n-C₃H₇ | |
| 10.64 | CF₃ | Cl | n-C₄H₉ | |
| 10.65 | CF₃ | Cl | sec.-C₄H₉ | 108–110 |
| 10.66 | CF₃ | Cl | i-C₄H₉ | 122–124 |

TABLE 10-continued

Compounds of the formula V where A is $A_6$ $A_6$—CO—NH—(phenyl with $R^7$)

| No. | $R^5$ | $R^6$ | $R^7$ | Phys. data mp [°C.] |
|---|---|---|---|---|
| 10.67 | $CF_3$ | Cl | tert.-$C_4H_9$ | |
| 10.68 | $CF_3$ | Cl | n-$C_5H_{11}$ | |
| 10.69 | $CF_3$ | Cl | sec.-$C_5H_{11}$ | |
| 10.70 | $CF_3$ | Cl | n-$C_6H_{13}$ | |
| 10.71 | $CF_3$ | Cl | n-$C_7H_{15}$ | |
| 10.72 | $CF_3$ | Cl | sec.-$C_7H_{15}$ | |
| 10.73 | $CF_3$ | Cl | Ethoxy | |
| 10.74 | $CF_3$ | Cl | Propoxy | |
| 10.75 | $CF_3$ | Cl | 1-Methylethoxy | |
| 10.76 | $CF_3$ | Cl | n-Butoxy | |
| 10.77 | $CF_3$ | Cl | 1-Methylpropoxy | |
| 10.78 | $CF_3$ | Cl | 2-Methylpropoxy | |
| 10.79 | $CF_3$ | Cl | 1,1-Dimethylethoxy | |
| 10.80 | $CF_3$ | Cl | n-Pentyloxy | |
| 10.81 | $CF_3$ | Cl | n-Hexyloxy | |
| 10.82 | $CF_3$ | Cl | Cyclopentyl | 113–115 |
| 10.83 | $CF_3$ | Cl | Cyclopentenyl | 132–133 |

TABLE 11

Compounds of the formula V where A is $A_7$ $A_7$—CO—NH—(phenyl with $R^7$)

| No. | $R^2$ | $R^6$ | $R^7$ | Phys. data mp [°C.] |
|---|---|---|---|---|
| 11.1 | H | $CH_3$ | i-$C_3H_7$ | |
| 11.2 | H | $CH_3$ | n-$C_3H_7$ | |
| 11.3 | H | $CH_3$ | n-$C_4H_9$ | |
| 11.4 | H | $CH_3$ | sec.-$C_4H_9$ | oil |
| 11.5 | H | $CH_3$ | i-$C_4H_9$ | oil |
| 11.6 | H | $CH_3$ | tert.-$C_4H_9$ | |
| 11.7 | H | $CH_3$ | n-$C_5H_{11}$ | |
| 11.8 | H | $CH_3$ | sec.-$C_5H_{11}$ | |
| 11.9 | H | $CH_3$ | n-$C_6H_{13}$ | |
| 11.10 | H | $CH_3$ | n-$C_7H_{15}$ | |
| 11.11 | H | $CH_3$ | sec.-$C_7H_{15}$ | |
| 11.12 | H | $CH_3$ | Ethoxy | |
| 11.13 | H | $CH_3$ | Propoxy | |
| 11.14 | H | $CH_3$ | 1-Methylethoxy | |
| 11.15 | H | $CH_3$ | n-Butoxy | |
| 11.16 | H | $CH_3$ | 1-Methylpropoxy | |
| 11.17 | H | $CH_3$ | 2-Methylpropoxy | |
| 11.18 | H | $CH_3$ | 1,1-Dimethylethoxy | |
| 11.19 | H | $CH_3$ | n-Pentyloxy | |
| 11.20 | H | $CH_3$ | n-Hexyloxy | |
| 11.21 | H | $CH_3$ | Cyclopentyl | |
| 11.22 | H | $CH_3$ | Cyclopentenyl | |

TABLE 12

Compounds of the formula V where A is $A_3$ (furan ring with $R^2$, $CH_3$, O, $CH_3$)—CO—NH—(phenyl with $R^7$)

| No | $R^2$ | $R^7$ | Phys. data mp [°C.] |
|---|---|---|---|
| 12.1 | H | i-$C_3H_7$ | 147–148 |
| 12.2 | H | n-$C_3H_7$ | |
| 12.3 | H | n-$C_4H_9$ | |
| 12.4 | H | sec.-$C_4H_9$ | 109–110 |
| 12.5 | H | i-$C_4H_9$ | 114–115 |
| 12.6 | H | tert.-$C_4H_9$ | |
| 12.7 | H | n-$C_5H_{11}$ | |
| 12.8 | H | sec.-$C_5H_{11}$ | |
| 12.9 | H | n-$C_6H_{13}$ | |
| 12.10 | H | n-$C_7H_{15}$ | |
| 12.11 | H | sec.-$C_7H_{15}$ | |
| 12.12 | H | Ethoxy | |
| 12.13 | H | Propoxy | |
| 12.14 | H | 1-Methylethoxy | |
| 12.15 | H | n-Butoxy | |
| 12.16 | H | 1-Methylpropoxy | |
| 12.17 | H | 2-Methylpropoxy | |
| 12.18 | H | 1,1-Dimethylethoxy | |
| 12.19 | H | n-Pentyloxy | |
| 12.20 | H | n-Hexyloxy | |
| 12.21 | H | Cyclopentyl | 97–98 |
| 12.22 | H | Cyclohexyl | 125–127 |
| 12.23 | H | 2-Cyclopentenyl | 98–99 |
| 12.24 | H | 1-Cyclopentenyl | |
| 12.25 | H | 2-Cyclohexenyl | 82–84 |
| 12.26 | H | 1-Cyclohexenyl | |
| 12.27 | H | Cyclopentyloxy | 73–75 |
| 12.28 | H | Cyclohexyloxy | |
| 12.29 | H | 2-Cyclopentenyloxy | |
| 12.30 | $CH_3$ | i-$C_3H_7$ | |
| 12.31 | $CH_3$ | n-$C_3H_7$ | |
| 12.32 | $CH_3$ | n-$C_4H_9$ | |
| 12.33 | $CH_3$ | sec.-$C_4H_9$ | 80–82 |
| 12.34 | $CH_3$ | i-$C_4H_9$ | 114–116 |
| 12.35 | $CH_3$ | tert.-$C_4H_9$ | |
| 12.36 | $CH_3$ | n-$C_5H_{11}$ | |
| 12.37 | $CH_3$ | sec.-$C_4H_9$ | |
| 12.38 | $CH_3$ | n-$C_6H_{13}$ | |
| 12.39 | $CH_3$ | n-$C_7H_{15}$ | |
| 12.40 | $CH_3$ | sec.-$C_7H_{15}$ | |
| 12.41 | $CH_3$ | Ethoxy | |
| 12.42 | $CH_3$ | Propoxy | |
| 12.43 | $CH_3$ | 1-Methylethoxy | |
| 12.44 | $CH_3$ | n-Butoxy | |
| 12.45 | $CH_3$ | 1-Methylpropoxy | |
| 12.46 | $CH_3$ | 2-Methylpropoxy | |
| 12.47 | $CH_3$ | 1,1-Dimethylethoxy | |
| 12.48 | $CH_3$ | n-Pentyloxy | |
| 12.49 | $CH_3$ | n-Hexyloxy | |
| 12.50 | $CH_3$ | Cyclopentyl | |
| 12.51 | H | 2-Methyl-2-propenyloxy | 40–41 |
| 12.52 | H | 1-Ethyl-propoxy | oil |
| 12.53 | H | 2-Cyclohexenyloxy | 51–53 |

Manufacturing examples

Example 7

At 0° C., 2.3 g of 2-methyl-4-trifluoromethyl-thiazole-5-carboxylic chloride is dripped into a solution of 1.4 g of 2-n-propylaniline and 1.1 g of triethylamine in 15 ml of tetrahydrofuran, and the mixture is stirred for 12 hours at 20° C.

After dilution with 300 ml of water, extraction with methyltert.-butyl ether (2×70 ml), evaporation of the solvent and mixture of the residue with a small amount of n-pentane, there is isolated 2.8 g of 2-methyl-4-trifluoromethyl-thiazole-5-carboxylic acid-2-n-propyl-anilide; m.p.: 114°–116° C. (Table 9, No. 2).

Example 8

At 0° C., 3.8 g of 1,3-dimethyl-5-chloroopyrazole-4-carboxylic chloride is dripped into a solution of 2.7 g of 2-isopropylamine and 2.2 g of triethylamine in 40 ml of dichloromethane, and the mixture is stirred for 2 hours at 0° C.

After washing with 50 ml of water, evaporation of the solvent and recrystallization from cyclohexane there is isolated 3.3 g of 1,3-dimethyl-5-chloropyrazole-4-carboxylic acid-2-isopropylanilide; m.p. 108°–110° C. (Table 10, No. 1).

TABLE 13

Compounds of the formula V where A is $A_1$

| No. | $R^1$ | $R^7$ | Phys. data mp [°C.] |
|---|---|---|---|
| 13.1 | Br | i-$C_3H_7$ | |
| 13.2 | Br | n-$C_3H_7$ | |
| 13.3 | Br | n-$C_4H_9$ | |
| 13.4 | Br | sec.-$C_4H_9$ | 74–75 |
| 13.5 | Br | i-$C_4H_9$ | 110–112 |
| 13.6 | Br | tert.-$C_4H_9$ | |
| 13.7 | Br | n-$C_4H_9$ | |
| 13.8 | Br | sec.-$_5H_{11}$ | |
| 13.9 | Br | n-$C_6H_{13}$ | |
| 13.10 | Br | n-$C_7H_{15}$ | |
| 13.11 | Br | sec.-$C_7H_{15}$ | |
| 13.12 | Br | 1-Methylvinyl | |
| 13.13 | Br | 2-Methylvinyl | |
| 13.14 | Br | Allyl | |
| 13.15 | Br | 2-Methylallyl | |
| 13.16 | Br | 2-Ethylallyl | |
| 13.17 | Br | 1-Methylallyl | |
| 13.18 | Br | l-Ethylallyl | |
| 13.19 | Br | 1-Methyl-2-butenyl | |
| 13.20 | Br | l-Ethyl-2-butenyl | |
| 13.21 | Br | 1-Isopropyl-2-butenyl | |
| 13.22 | Br | 1-n-Butyl-2-butenyl | |
| 13.23 | Br | 1-Methyl-2-pentenyl | |
| 13.24 | Br | 1,4-Dimethyl-2-pentenyl | |
| 13.25 | Br | Propargyl | |
| 13.26 | Br | 2-butynyl | |
| 13.27 | Br | 3-butynyl | |
| 13.28 | Br | Ethoxy | |
| 13.29 | Br | Propoxy | |
| 13.30 | Br | 1-Methylethoxy | |
| 13.31 | Br | n-Butoxy | |
| 13.32 | Br | 1-methylpropoxy | |
| 13.33 | Br | 2-Methylpropoxy | |

TABLE 13-continued

Compounds of the formula V where A is $A_1$

| No. | $R^1$ | $R^7$ | Phys. data mp [°C.] |
|---|---|---|---|
| 13.34 | Br | 1,1-Dimethylethoxy | |
| 13.35 | Br | n-Pentyloxy | |
| 13.36 | Br | n-Hexyloxy | |
| 13.37 | Br | 2-Ethylhexyloxy | |
| 13.38 | Br | 2-Propenyloxy | |
| 13.39 | Br | 2-Butentyloxy | |
| 13.40 | Br | 2-Methyl-2-propenyloxy | |
| 13.41 | Br | 2-Pentenyloxy | |
| 13.42 | Br | 3-Pentenyloxy | |
| 13.43 | Br | 3-chloro-2-propenyloxy | |
| 13.44 | Br | 2,3-Dichloro-2-propenyloxy | |
| 13.45 | Br | 2,3,3-Tri-chloro-propenyloxy | |
| 13.46 | Br | 2-propynyloxy | |
| 13.47 | Br | 2-butynyl-oxy | |
| 13.48 | Br | 3-butynyl-oxy | |
| 13.49 | Br | 1-Methyl-2-propynyloxy | |
| 13.50 | Br | Cyclopropyl | |
| 13.51 | Br | Cyclobutyl | |
| 13.52 | Br | Cyclopentyl | |
| 13.53 | Br | Cyclohexyl | |
| 13.54 | Br | 2-Cyclopentenyl | |
| 13.55 | Br | 1-Cyclopentenyl | |
| 13.56 | Br | 2-Cyclohexenyl | |
| 13.57 | Br | 1-Cyclohexenyl | |
| 13.58 | Br | Cyclopentyloxy | |
| 13.59 | Br | Cyclohexyloxy | |
| 13.60 | Br | 2-Cyclopentenyloxy | |
| 13.61 | Br | 2-Cyclohexenyloxy | |

TABLE 14

Compounds of the formula V where A is $A_1$

| No. | $R^1$ | $R^7$ | Phys. data mp [°C.] |
|---|---|---|---|
| 14.1 | I | i-$C_3H_7$ | |
| 14.2 | I | n-$C_3H_7$ | |
| 14.3 | I | n-$C_3H_7$ | |
| 14.4 | I | sec.-$C_4H_9$ | 97–98 |
| 14.5 | I | i-$C_4H_9$ | 148–149 |
| 14.6 | I | tert.-$C_4H_9$ | |
| 14.7 | I | n-$C_5H_{11}$ | |
| 14.8 | I | sec.-$C_5H_{11}$ | |
| 14.9 | I | n-$C_6H_{12}$ | |
| 14.10 | I | n-$C_7H_{15}$ | |
| 14.11 | I | sec.-$C_7H_{15}$ | |
| 14.12 | I | 1-Methylvinyl | |
| 14.13 | I | 2-Methylvinyl | |
| 14.14 | I | Allyl | |
| 14.15 | I | 2-Methylallyl | |
| 14.16 | I | 2-Ethylallyl | |
| 14.17 | I | 1-Methylallyl | |
| 14.18 | I | 1-Ethylallyl | |

TABLE 14-continued

Compounds of the formula V where A is $A_1$ $A_1$—CO—NH—C$_6$H$_4$—$R^7$

| No. | $R^1$ | $R^7$ | Phys. data mp [°C.] |
|---|---|---|---|
| 14.19 | I | 1-Methyl-2-butenyl | |
| 14.20 | I | 1-Ethyl-2-butenyl | |
| 14.21 | I | 1-Isopropyl-2-butenyl | |
| 14.22 | I | 1-n-Butyl-2-butenyl | |
| 14.23 | I | 1-Methyl-2-pentenyl | |
| 14.24 | I | 1,4-Dimethyl-2-pentenyl | |
| 14.25 | I | Propargyl | |
| 14.26 | I | 2-butynyl | |
| 14.27 | I | 3-butynyl | |
| 14.28 | I | Ethoxy | |
| 14.29 | I | Propoxy | |
| 14.30 | I | 1-Methylethoxy | |
| 14.31 | I | n-Butoxy | |
| 14.31 | I | 1-Methylpropoxy | |
| 14.33 | I | 2-Methylpropoxy | |
| 14.34 | I | 1,1-Dimethylethoxy | |
| 14.35 | I | n-Pentyloxy | |
| 14.36 | I | n-Hexyloxy | |
| 14.37 | I | 2-Ethylhexyloxy | |
| 14.38 | I | 2-Propenyloxy | |
| 14.39 | I | 2-Butentyloxy | |
| 14.40 | I | 2-Methyl-2-propenyloxy | |
| 14.41 | I | 2-Pentenyloxy | |
| 14.42 | I | 3-Pentenyloxy | |
| 14.43 | I | 3-chloro-2-propenyloxy | |
| 14.44 | I | 2,3-Dichloro-2-propenyloxy | |
| 14.45 | I | 2,3,3-Trichloro.-propenyloxy | |
| 14.46 | I | 2-propynyloxy | |
| 14.47 | I | 2-butynyl-oxy | |
| 14.48 | I | 3-butynyl-oxy | |
| 14.49 | I | 1-Methyl-2-propynyloxy | |
| 14.50 | I | Cyclopropyl | |
| 14.51 | I | Cyclobutyl | |
| 14.52 | I | Cyclopentyl | |
| 14.53 | I | Cyclohexyl | |
| 14.54 | I | 2-Cyclopentenyl | |
| 14.55 | I | 1-Cyclopentenyl | |
| 14.56 | I | 2-Cyclohexenyl | |
| 14.57 | I | 1-Cyclohexenyl | |
| 14.58 | I | Cyclopentyloxy | |
| 14.59 | I | Cyclohexyloxy | |
| 14.60 | I | 2-Cyclopentenyloxy | |
| 14.61 | I | 2-Cyclohexenyloxy | |

TABLE 15

Compounds of the formula V where A is $A_3$

| No. | $R^7$ | Phys. data mp [°C.] |
|---|---|---|
| 15.1 | i-C$_3$H$_7$ | |
| 15.2 | n-C$_3$H$_7$ | |
| 15.3 | n-C$_4$H$_9$ | |
| 15.4 | sec.-C$_4$H$_9$ | 78–80 |
| 15.5 | i-C$_4$H$_9$ | |
| 15.6 | tert.-C$_4$H$_9$ | 106–107 |
| 15.7 | n-C$_5$H$_{11}$ | |
| 15.8 | sec.-C$_5$H$_{11}$ | |
| 15.9 | n-C$_6$H$_{13}$ | |
| 15.10 | n-C$_7$H$_{15}$ | |
| 15.11 | sec.-C$_7$H$_{15}$ | |
| 15.12 | Ethoxy | |
| 15.13 | Propoxy | |
| 15.14 | 1-Methylethoxy | |
| 15.15 | n-Butoxy | |
| 15.16 | 1-Methylpropoxy | |
| 15.17 | 2-Methylpropoxy | |
| 15.18 | 1,1-Dimethylethoxy | |
| 15.19 | n-Pentyloxy | |
| 15.20 | n-Hexyloxy | |
| 15.21 | cyclopentyl | |
| 15.22 | Cyclohexyl | |
| 15.23 | 2-Cyclopentenyl | |
| 15.24 | 1-Cyclopentenyl | |
| 15.25 | 2-Cyclohexenyl | |
| 15.26 | 1-Cyclohexenyl | |
| 15.27 | Cyclopentyloxy | |
| 15.28 | Ethoxy | |
| 15.29 | Propoxy | |
| 15.30 | 1-Methylethoxy | |
| 15.31 | n-Butoxy | |
| 15.32 | 1-Methylpropoxy | |
| 15.33 | 2-Methylpropoxy | |
| 15.34 | 1,1-Dimethylethoxy | |
| 15.35 | n-Pentyloxy | |
| 15.36 | n-Hexyloxy | |
| 15.37 | 2-Ethylhexyloxy | |
| 15.38 | 2-Propenyloxy | |
| 15.39 | 2-Butentyloxy | |
| 15.40 | 2-Methyl-2-propenyloxy | oil |
| 15.41 | 2-Pentenyloxy | |
| 15.42 | 3-Pentenyloxy | |
| 15.43 | 3-chloro-2-propenyloxy | |
| 15.44 | 2,3-Dichloro-2-propenyloxy | |
| 15.45 | 2,3,3-Trichloropropenyloxy | |
| 15.46 | 2-Propynyloxy | |
| 15.47 | 2-Butynyl-oxy | |
| 15.48 | 3-Butynyl-oxy | |
| 15.49 | 1-Methyl-2-propynyloxy | |
| 15.50 | Cyclopropyl | |
| 15.51 | Cyclobutyl | |
| 15.52 | Cyclopentyl | |
| 15.53 | Cyclohexyl | |
| 15.54 | 2-Cyclopentenyl | |
| 15.55 | 1-Cyclopencenyl | |
| 15.56 | 2-Cyclohexenyl | |
| 15.57 | 1-Cyclohexenyl | |
| 15.58 | Cyclopentyloxy | oil |
| 15.59 | Cyclohexyloxy | |
| 15.60 | 2-Cyclopentenyloxy | |
| 15.61 | 2-Cyclohexenyloxy | oil |
| 15.62 | 1-Ethylpropoxy | oil |

The invention further relates to the following novel compounds.

Nicotinic anilide derivatives of the general formula I

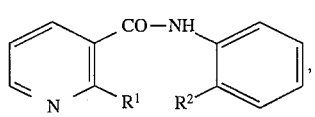

where the substituents have the following meanings:

$R^1$ halogen, methyl, trifluoromethyl, methoxy, methylthio, methylsulfinyl, methylsulfonyl, $R^2$ unsubstituted or halogen-substituted $C_3$–$C_{12}$-alkyl, unsubstituted or halogen-substituted $C_3$–$C_{12}$-alkenyl $C_3$–$C_6$-alkynyl, unsubstituted or halogen-substituted $C_2$–$C_{12}$-alkoxy, unsubstituted or halogen-substituted $C_3$–$C_{12}$-alkenyloxy, $C_3$–$C_{12}$-alkynyloxy, $C_3$–$C_6$-cycloalkyl, $C_4$–$C_6$-cycloalkenyl, $C_5$–$C_6$-cycloalkyloxy, $C_5$–$C_6$-cycloalkenyloxy, with the proviso that $R^2$ is not isopropyl when $R^1$ is chlorine.

Anilide derivatives of the general formula II

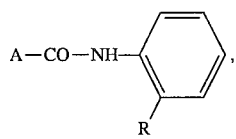

where the substituents have the following meanings:

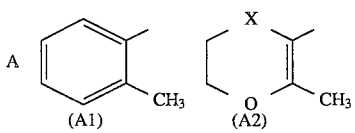

X methylene or sulfur

R unsubstituted or halogen-substituted $C_3$–$C_{12}$-alkyl, unsubstituted or halogen-substituted $C_3$–$C_{12}$-alkenyl, $C_3$–$C_6$-alkynyl, unsubstituted or halogen-substituted $C_2$–$C_{12}$-alkoxy, unsubstituted or halogen-substituted $C_3$–$C_{12}$-alkenyloxy, $C_3$–$C_{12}$-alkynyloxy, unsubstituted or $C_1$–$C_4$-alkyl-substituted $C_3$–$C_6$-cycloalkyl, unsubstituted or $C_1$–$C_4$-alkyl-substituted $C_4$–$C_6$-cycloalkenyl, unsubstituted or $C_1$–$C_4$-alkyl-substituted $C_4$–$C_6$-cycloalkyloxy, unsubstituted or $C_1$–$C_4$-alkyl-substituted $C_5$–$C_6$-cycloalkyloxy, unsubstituted or $C_1$–$C_4$-alkyl-substituted $C_5$–$C_6$-cycloalkenloxy with the proviso that A is not $A_1$ when R is ethoxy, isopropoxy or allyloxy, A is not $A_2$, X denoting sulfur, when R is ethoxy, propoxy, n-butoxy, sec.-butoxy or n-pentyloxy, A is not $A_2$, X denoting methylene, when R is isopropyl.

2-Aminobiphenyl derivatives of the general formula III,

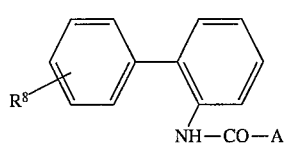

where the substituents have the following meanings:

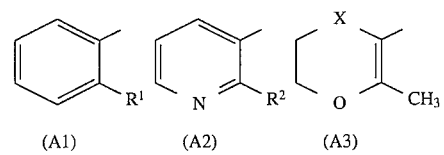

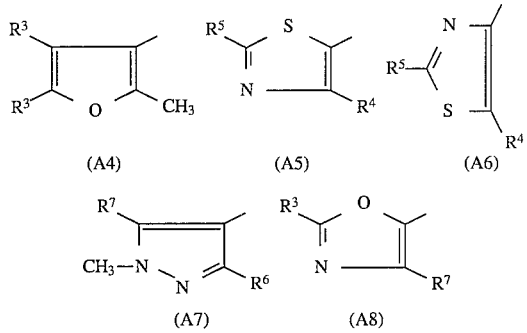

X methylene, sulfur, sulfinyl, sulfonyl ($SO_2$), $R^1$ methyl, trifluoromethyl, chlorine, bromine, iodine, $R^2$ trifluoromethyl, chlorine $R^3$ hydrogen or methyl $R^4$ methyl, trifluoromethyl, chlorine $R^5$ hydrogen, methyl, chlorine $R^6$ methyl, trifluoromethyl $R^7$ methyl, chlorine $R^8$ $C_1$–$C_4$-alkoxy, $C_1$–$C_4$-alkylthio, halogen.

Carboxanilide derivatives of the general formula V

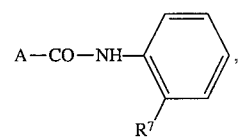

where the substituents have the following meanings:

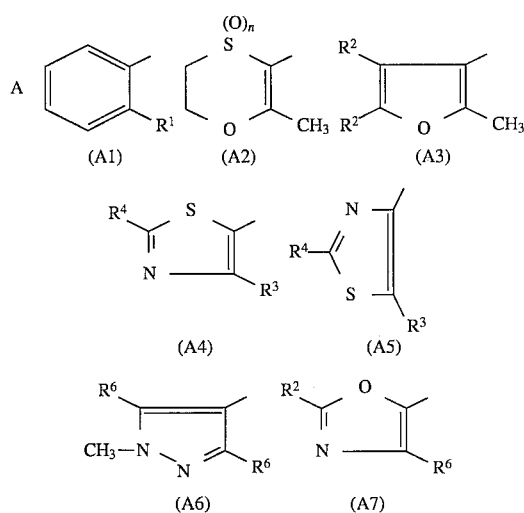

n 1 or 2

$R^1$ trifluoromethyl, chlorine, bromine, iodine, $R^2$ hydrogen or methyl $R^3$ methyl, trifluoromethyl, chlorine $R^4$ hydrogen, methyl, chlorine $R^5$ methyl, trifluoromethyl $R^6$ methyl, chlorine $R^7$ unsubstituted or halogen-substituted $C_3$–$C_{12}$-alkyl, unsubstituted or halogen-substituted $C_3$–$C_{12}$-alkenyl, $C_3$–$C_6$-alkynyl, unsubstituted or halogen-substituted $C_2$–$C_{12}$-alkoxy, unsubstituted or halogen-substituted $C_3$–$C_{12}$-alkenyloxy, $C_3$–$C_{12}$-alkynyloxy, unsubstituted or $C_1$–$C_4$-alkyl-substituted $C_3$–$C_6$-cycloalkyl, unsubstituted or $C_1$–$C_4$-alkyl-substituted $C_4$–$C_6$-cycloalkenyl, unsubstituted or $C_1$–$C_4$-alkyl-substituted $C_5$–$C_6$-cycloalkyloxy, unsubstituted or $C_1$–$C_4$-alkyl-substituted $C_5$–$C_6$-cycloalkenyloxy, with the proviso that $R^7$ is not 3-methylbut-2-en-1-yl or 3-methyl- but-3-en-1-yl when $R^1$ is trifluoromethyl.

The novel compounds are suitable as fungicides.

The fungicidal compounds according to the invention, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the plants are sprayed or dusted with the active ingredients, or the seeds of the plants are treated with the active ingredients.

The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methyl cellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of formulations are given below.

I. A solution of 90 parts by weight of compound no. 1.7 and 10 parts by weight of N-methyl-α-pyrrolidone, which is suitable for application in the form of very fine drops.

II. A mixture of 20 parts by weight of compound no. 1.8, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 1.3, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound no. 1.4, 25 parts by weight of cyclohexanol, 65 parts by weight of a mineral oil fraction having a boiling point between 210 and 280° C., and 10 parts by weight of the adduct of 40 moles of ethylene oxide and 1 mole of castor oil.

V. A hammer-milled mixture of 80 parts by weight of compound no. 1.5, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 1.7 and 97 parts by weight of particulate kaolin. The dust contains 3wt % of the active ingredient.

VII. An intimate mixture of 30 parts by weight of compound no. 1.8, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 1.9, 10 parts by weight of the sodium salt of a phenolsulfonic acid-urea-formaldehyde condensate, 2 parts by weight of silica gel and 48 parts by weight of water, which dispersion can be further diluted.

IX. A stable oily dispersion of 20 parts by weight of compound no. 1.33, 2 parts by weight of the calcium salt of dodecylbenzenesulfonic acid, 8 parts by weight of a fatty alcohol polyglycol ether, 20 parts by weight of the sodium salt of a phenolsulfonic acid-urea-formaldehyde condensate and 68 parts by weight of a paraffinic mineral oil.

The novel compounds are extremely effective on a broad spectrum of phytopathogenic fungi, in particular Botrytis. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The compounds are applied by treating the fungi or the seeds, plants or materials threatened by fungus attack, or the soil with a fungicidally effective amount of the active ingredients.

The agents may be applied before or after infection of the materials, plants or seeds by the fungi.

The novel compounds are particularly useful for controlling the following plant diseases:

*Erysiphe graminis* in cereals,

*Erysiphe cichoracearum* and *Sphaerotheca fuliginea* in cucurbits,

*Podosphaera leucotricha* in apples,

*Uncinula necator* in vines,

*Venturia inaequalis* (scab) in apples,

Helminthosporium species in cereals,

*Septoria nodorum* in wheat,

*Botrytis cinerea* (gray mold) in strawberries and grapes,

*Cercospora arachidicola* in groundnuts,

*Pseudocercosporella herpotrichoides* in wheat and barley,

*Pyricularia oryzae* in rice,

Fusarium and Verticillium species in various plants,

Alternaria species in fruit and vegetables.

Use against Botrytis is preferred.

The novel compounds may also be used for protecting materials (timber), e.g., against *Paecilomyces variotii*.

The fungicidal agents generally contain from 0.1 to 95, and preferably from 0.5 to 90, wt % of active ingredient.

The application rates depend on the type of effect desired, and range from 0.02 to 3 kg of active ingredient per hectare.

When the active ingredients are used for treating seed, rates of 0.001 to 50, and preferably from 0.01 to 10, g per kg of seed are generally sufficient.

In these application forms, the agents according to the invention may also be present together with other active ingredients, for example herbicides, insecticides, growth regulators, and other fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:

sulfur, dithiocarbamates and their derivatives, such as
 ferric dimethyldithiocarbamate,
 zinc dimethyldithiocarbamate,
 zinc ethylenebisdithiocarbamate,
 manganese ethylenebisdithiocarbamate,
 manganese zinc ethylenediaminebisdithiocarbamate,
 tetramethylthiuram disulfides,
 ammonia complex of zinc N,N'-ethylenebisdithiocarbamate,
 ammonia complex of zinc N,N'-propylenebisdithiocarbamate,
 zinc N,N'-propylenebisdithiocarbamate and
 N,N'-polypropylenebis(thiocarbamyl) disulfide;

nitro derivatives, such as
 dinitro(1-methylheptyl)-phenyl crotonate,
 2-sec-butyl-4,6-dinitrophenyl 3,3-dimethylacrylate,
 2-sec-butyl-4,6-dinitrophenyl isopropylcarbonate and
 diisopropyl 5-nitroisophthalate;

heterocyclic substances, such as
 2-heptadecylimidazol-2-yl acetate,
 2,4-dichloro-6-(o-chloroanilino)-s-triazine,
 O,O-diethyl phthalimidophosphonothioate,
 5-amino-1-[-bis-(dimethylamino)-phosphinyl]-3-phenyl-1,2,4-triazole,
 2,3-dicyano-1,4-dithioanthraquinone,
 2-thio-1,3-dithio[4,5-b]quinoxaline,
 methyl 1-(butylcarbamyl)-2-benzimidazolecarbamate,
 2-methoxycarbonylaminobenzimidazole,
 2-(fur-2-yl)-benzimidazole,
 2-(thiazol-4-yl)benzimidazole,
 N-(1,1,2,2-tetrachloroethylthio)-tetrahydrophthalimide,
 N-trichloromethylthiotetrahydrophthalimide,
 N-trichloromethylthiophthalimide,
 N-dichlorofluoromethylthio-N', N'-dimethyl-N-phenylsulfuric acid diamide,
 5-ethoxy-3-trichloromethyl-1,2,3-thiadiazole,
 2-thiocyanatomethylthiobenzothiazole,
 1,4-dichloro-2,5-dimethoxybenzene,
 4-(2-chlorophenylhydrazono)-3-methyl -5-isoxazolone,
 2-thiopyridine 1-oxide,
 8-hydroxyquinoline and its copper salt,
 2,3-dihydro-5-carboxanilido-6-methyl-1,4-oxathiyne,
 2,3-dihydro-5-carboxanilido-6-methyl-1,4-oxathiyne 4,4-dioxide,
 2-methyl-5,6-dihydro-4H-pyran-3-carboxanilide,
 2-methylfuran-3-carboxanilide,
 2,5-dimethylfuran-3-carboxanilide,
 2,4,5-trimethylfuran-3-carboxanilide,
 2,5-dimethyl-N-cyclohexylfuran-3-carboxamide,
 N-cyclohexyl-N-methoxy-2,5-diethylfuran-3-carboxamide,
 2-methylbenzanilide,
 2-iodobenzanilide,
 N-formyl-N-morpholine-2,2,2-trichloroethylacetal,
 piperazine-1,4-diylbis-(1-(2,2,2-trichloroethyl)-formamide),
 1-(3,4-dichloroanilino)-1-formylamino-2,2,2-trichloroethane,
 2,6-dimethyl-N-tridecylmorpholine and its salts,
 2,6-dimethyl-N-cyclododecylmorpholine and its salts,
 N [3-(p-tert.-butylphenyl) -2-methylpropyl]-cis-2,6-dimethylmorpholine
 N-3-(p-tert.-butylphenyl) -2-methylpropyl'-piperidine,
 1-2-(2,4-dichlorophenyl) -4-ethyl-1,3-dioxolan-2-yl-ethyl'-1H-1,2,4-triazole, 1-[2-(2,4-dichlorophenyl) -4-n-propyl-1,3-dioxolan-2-yl-ethyl]-1H-1,2,4-triazole,
N-(n-propyl)-N-(2,4,6-trichlorophenoxyethyl)-N'-imidazolylurea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-(2-dimethylamino-4-hydroxy-6-methylpyrimidine,
bis -(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl- 3-chloro-2-aminopyridine, and
1-((bis-(4-fluorophenyl)-methylsilyl)-methyl)-1H-1,2,4-triazole.

USE EXAMPLES

The active ingredients 2-chloronicotic acid-2'-ethylanilide (A)—disclosed in U.S. Pat. No. 4,001,416—and 2-chloronicotic acid-3'-isopropylanilide (B)—disclosed in DE 26 11 601 —were used for comparison purposes.

USE EXAMPLE 1

Action on *Botrytis cinerea* in paprika

Slices of green paprika pods were sprayed to runoff with aqueous suspensions containing (dry basis) 80% of active ingredient and 20% of emulsifier. Two hours after the sprayed-on layer had dried, the slices were inoculated with a spore suspension of the fungus *Botrytis cinerea*, which contained $1.7 \times 10^6$ spores per ml of a 2% strength malt solution. The inoculated slices were then incubated in humid chambers at 18° C. for 4 days. The development of Botrytis on the slices attacked was then assessed visually.

The results show that active ingredients 1.5, 1.7 and 1.8, applied as spray liquors containing 500 ppm of active ingredient, have a better fungicidal action (95%) than prior art comparative compounds A (10%) and B (65%).

USE EXAMPLE 2

Action on *Botrytis cinerea* in paprika

Paprika pods were slit open and the inside surfaces were sprayed to runoff with aqueous active ingredient formulations containing (dry basis) 80% of active ingredient and 20% of emulsifier. After the sprayed-on layer had dried, the pieces were inoculated with an aqueous suspension containing $1.7 \times 10^6$ spores of *Botrytis cinerea* per ml.

The paprika pieces were then kept for 4 days in climatic cabinets at 20°–22° C. The extent of fungus spread was then assessed visually.

The results show that compounds 2.4, 4.4, 6.4, 7.4, 7.5, 9.1, 9.2, 9.4, 9.5, 10.1, 10.2, 10.4, 10.5, 12.4, 12.6, 2.65 and 2.66, applied as aqueous spray liquors containing 1,000 ppm of active ingredient, have a good fungicidal action (100%).

We claim:

1. A method for treating Botrytis infestation comprising applying to a subject in need thereof, an effective amount of a compound of formula $$A-CO-NH-\text{Ar}(R)$$

wherein A has the following meaning:
thiazol-5-yl substituted in the 2- and 4-positions by hydrogen, methyl, chlorine or trifluoromethyl; and R has the following meanings: unsubstituted $C_3$–$C_{12}$-alkyl, unsubstituted $C_3$–$C_{12}$-alkenyl, $C_3$–$C_6$-alkynyl, unsubstituted $C_3$–$C_{12}$-alkenyloxy, $C_3$–$C_{12}$-alkynyloxy, unsubstituted or $C_1$–$C_4$-alkyl-substituted $C_3$–$C_6$-cycloalkyl, unsubstituted or $C_1$–$C_4$-alkyl-substituted $C_4$–$C_6$-cycloalkenyl, unsubstituted or $C_1$–$C_4$-alkyl substituted $C_5$–$C_6$-cycloalkyloxy, unsubstituted or $C_1$–$C_4$-alkyl substituted $C_5$–$C_6$-cycloalkenyloxy, or phenyl which is unsubstituted or substituted by $C_1$–$C_4$-alkyl, $C_1$–$C_4$-alkoxy, $C_3$–$C_4$alkylthio or halogen;
in a suitable carrier.

2. A method for treating Botrytis infestation comprising applying to a subject in need thereof, an effective amount of a 2-aminobiphenyl compound of formula III $$R^8\text{-biphenyl-}NH-CO-A \quad \text{III}$$

wherein A has the following meaning:

$$\underset{N}{\overset{R^5}{\underset{\|}{\diagup}}} \overset{S}{\diagdown} R^4 \quad (A5)$$

$R^4$ methyl, trifluoromethyl, or chlorine;
$R^5$ is hydrogen, methyl, or chlorine; and
$R^8$ is $C_1$–$C_4$-alkyl, $C_1$–$C_4$-alkoxy, $C_1$–$C_4$-alkylthio or halogen; in a suitable carrier.

3. A method for treating Botrytis infestation comprising applying to a subject in need thereof, an effective amount of a 2-aminobiphenyl compound of formula IV

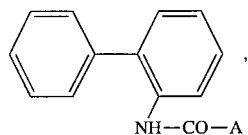   IV wherein A has the following meaning:

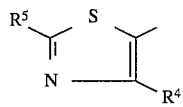   (A5)

wherein $R^4$ and $R^5$ are as follows:

$R^4$ is methyl and $R^5$ is hydrogen; or $R^4$ is methyl and $R^5$ is chlorine; or $R^4$ is trifluoromethyl and $R^5$ is hydrogen; or R4 is trifluoromethyl and $R^5$ is methyl; or R4 is trifluoromethyl and $R^5$ is chlorine; or $R^4$ is chlorine and $R^5$ is hydrogen; or $R^4$ is chlorine and $R^5$ is methyl; or $R^4$ is chlorine and $R^5$ is chlorine;

in a suitable carrier.

4. A method for treating Botrytis infestation comprising applying to a subject in need thereof, an effective amount of a carboxanilide compound of formula V

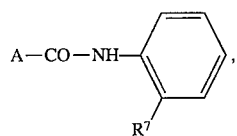   V wherein A has the following meaning:

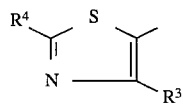   (A4)

$R^3$ is methyl, trifluoromethyl, or chlorine;

$R^4$ is hydrogen, methyl, or chlorine; and $R^7$ is unsubstituted $C_3$–$C_{12}$-alkyl, unsubstituted $C_3$–$C_{12}$-alkenyl, $C_3$–$C_6$-alkynyl, unsubstituted $C_3$–$C_{12}$-alkenyloxy, $C_3$–$C_{12}$-alkynyloxy, unsubstituted or $C_1$–$C_4$-alkyl-substituted $C_3$–$C_6$-cycloalkyl, unsubstituted or $C_1$–$C_4$-alkyl-substituted $C_4$–C6-cycloalkenyl, unsubstituted or $C_1$–$C_4$-alkyl-substituted $C_5$–$C_6$-cycloalkyloxy, unsubstituted or $C_1$–$C_4$-alkyl substituted $C_5$–$C_6$-cycloalkenyloxy, in a suitable carrier.

5. Aminobiphenyl compounds of formula III

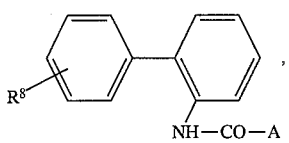   (III)

wherein A has the following meaning:

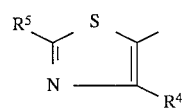   (A5)

R4 is methyl, trifluoromethyl, or chlorine;

$R^5$ is hydrogen, methyl, or chlorine; and $R^8$ is $C_1$–$C_4$-alkyl, $C_1$–$C_4$-alkoxy, $C_1$–$C_4$-alkylthio, halogen.

6. Aminobiphenyl compounds of formula IV

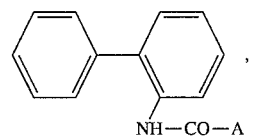   IV wherein A has the following meaning:

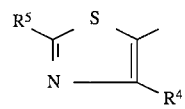   (A5)

wherein $R^4$ and $R^5$ are as follows:

$R^4$ is methyl and $R^5$ is hydrogen; or $R^4$ is methyl and $R^5$ is chlorine; or $R^4$ is trifluoromethyl and $R^5$ is hydrogen; or R4 is trifluoromethyl and $R^5$ is methyl; or $R^4$ is trifluoromethyl and $R^5$ is chlorine; or $R^4$ is chlorine and $R^5$ is hydrogen; or $R^4$ is chlorine and $R^5$ is methyl; or $R^4$ is chlorine and $R^5$ is chlorine.

7. Carboxanilide compounds of formula V

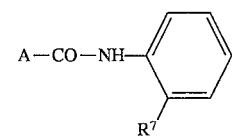

wherein A has the following meaning:

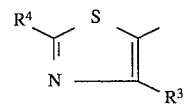   (A4)

$R^3$ is methyl, trifluoromethyl, or chlorine;

$R^4$ is hydrogen, methyl, or chlorine; and $R^7$ is unsubstituted $C_3$–$C_{12}$-alkyl, unsubstituted $C_3$–$C_{12}$-alkenyl, $C_3$–$C_6$-alkynyl, unsubstituted $C_3$–$C_{12}$-alkenyloxy, $C_3$–$C_{12}$-alkynyloxy, unsubstituted or $C_1$–$C_4$-alkyl-substituted $C_3$–$C_6$-cycloalkyl, unsubstituted or $C_1$–$C_4$-alkyl-substituted $C_4$–$C_6$-cycloalkenyl, unsubstituted or $C_1$–$C_4$-alkyl-substituted $C_5$–$C_6$-cycloalkyloxy, unsubstituted or $C_1$–$C_4$-alkyl-substituted $C_5$–$C_6$-cycloalkenyloxy, with the proviso that $R^7$ is not 3-methyl-but-2-en-1-yl or 3-methyl-but-3-en-1-yl when $R^1$ is trifluoromethyl.

8. A composition for treating Botrytis infestation comprising an effective amount of a compound of formula $$A-CO-NH-\underset{R}{\underset{|}{C_6H_4}}$$

wherein A has the following meaning:
thiazol-5-yl substituted in the 2- and 4-positions by hydrogen, methyl, chlorine or trifluoromethyl; and
R has the following meanings: unsubstituted $C_3$–$C_{12}$-alkyl, unsubstituted $C_3$–$C_{12}$-alkenyl, $C_3$–$C_6$-alkynyl, unsubstituted $C_3$–$C_{12}$-alkenyloxy, $C_3$–$C_{12}$-alkynyloxy, unsubstituted or $C_1$–$C_4$-alkyl-substituted $C_3$–$C_6$-cycloalkyl, unsubstituted or $C_1$–$C_4$-alkyl-substituted $C_4$–$C_6$-cycloalkenyl, unsubstituted or $C_1$–$C_4$-alkyl substituted $C_5$–$C_6$-cycloalkyloxy, unsubstituted or $C_1$–$C_4$-alkyl substituted $C_5$–$C_6$-cycloalkenyloxy, or phenyl which is substituted by $C_1$–$C_4$-alkyl, $C_4$–$C_6$-alkoxy, $C_1$–$C_4$-alkylthio or halogen;
in a suitable carrier.

9. A composition for treating Botrytis infestation comprising an effective amount of a 2-aminobiphenyl compound of claim 5 in a suitable carrier.

10. A composition for treating Botrytis infestation comprising an effective amount of a 2-aminobiphenyl compound of claim 6 in a suitable carrier.

11. A composition for treating Botrytis infestation comprising an effective amount of a carboxanilide compound of claim 7 in a suitable carrier.

* * * * *